United States Patent
Otsuka et al.

(10) Patent No.: US 10,547,753 B2
(45) Date of Patent: Jan. 28, 2020

(54) OPTICAL SCANNING DEVICE, TRANSPORT DEVICE, FEATURE DETECTION DEVICE, MEDIUM DETERMINATION DEVICE, SORTING DEVICE, AND MEDIUM SCANNING METHOD

(71) Applicant: SEIKO EPSON CORPORATION, Tokyo (JP)

(72) Inventors: Shuji Otsuka, Shiojiri (JP); Seiichi Taniguchi, Asahi-Mura (JP)

(73) Assignee: Seiko Epson Corporation, Tokyo (JP)

( * ) Notice: Subject to any disclaimer, the term of this patent is extended or adjusted under 35 U.S.C. 154(b) by 282 days.

(21) Appl. No.: 15/465,736

(22) Filed: Mar. 22, 2017

(65) Prior Publication Data
US 2017/0279977 A1    Sep. 28, 2017

(30) Foreign Application Priority Data

Mar. 25, 2016 (JP) ................................. 2016-061170
Dec. 13, 2016 (JP) ................................. 2016-240870

(51) Int. Cl.
*B65H 7/02* (2006.01)
*H04N 1/00* (2006.01)
(Continued)

(52) U.S. Cl.
CPC .......... *H04N 1/00058* (2013.01); *B41J 29/38* (2013.01); *B65H 7/00* (2013.01);
(Continued)

(58) Field of Classification Search
CPC ......... H04N 1/002885; H04N 1/02885; B65H 7/14; B41J 13/0009; B41J 11/00095; B41J 11/0095
See application file for complete search history.

(56) References Cited

U.S. PATENT DOCUMENTS 6,037,582 A * 3/2000 Youngers ........... H04N 1/02815
                                                    250/234
6,049,433 A * 4/2000 Tsai .......................... F21V 5/04
                                                    355/35

(Continued)

FOREIGN PATENT DOCUMENTS

JP          09318320 A  * 12/1997
JP       2007-303975 A    11/2007

*Primary Examiner* — Howard J Sanders
(74) *Attorney, Agent, or Firm* — Workman Nydegger

(57) ABSTRACT

An optical scanning device includes a reflected-light passing unit having a passing region through which a portion of reflected light that is the scanning light reflected by the medium passes. An outer peripheral contour line of the passing region includes a contour curve configured with a set of points where coordinates in a direction orthogonal to a scanning direction are uniquely determined for the coordinates in the scanning direction. The contour curve renders a curve protruded toward the passing region. When a region in contact with the contour curve in the passing region is divided into a plurality of quadrilateral minute regions having equivalent areas and extending from the contour curve to a predetermined coordinate position in the scanning direction and are continuously arranged in the orthogonal direction, widths of the minute regions in the scanning direction are different for each location in the orthogonal direction.

18 Claims, 26 Drawing Sheets

(51) Int. Cl.
*B41J 29/38* (2006.01)
*B65H 7/00* (2006.01)
*G01N 21/86* (2006.01)

(52) U.S. Cl.
CPC ............... *B65H 7/02* (2013.01); *G01N 21/86* (2013.01); *H04N 1/00037* (2013.01); *H04N 1/0075* (2013.01); *H04N 1/00665* (2013.01); *H04N 1/00724* (2013.01); *G01N 2021/8663* (2013.01)

(56) References Cited

U.S. PATENT DOCUMENTS

| | | | | |
|---|---|---|---|---|
| 6,637,894 B2 * | 10/2003 | Dewald | ................ | G02B 13/16 353/97 |
| 2003/0147052 A1 * | 8/2003 | Penn | ................ | G02B 26/0841 353/31 |

* cited by examiner

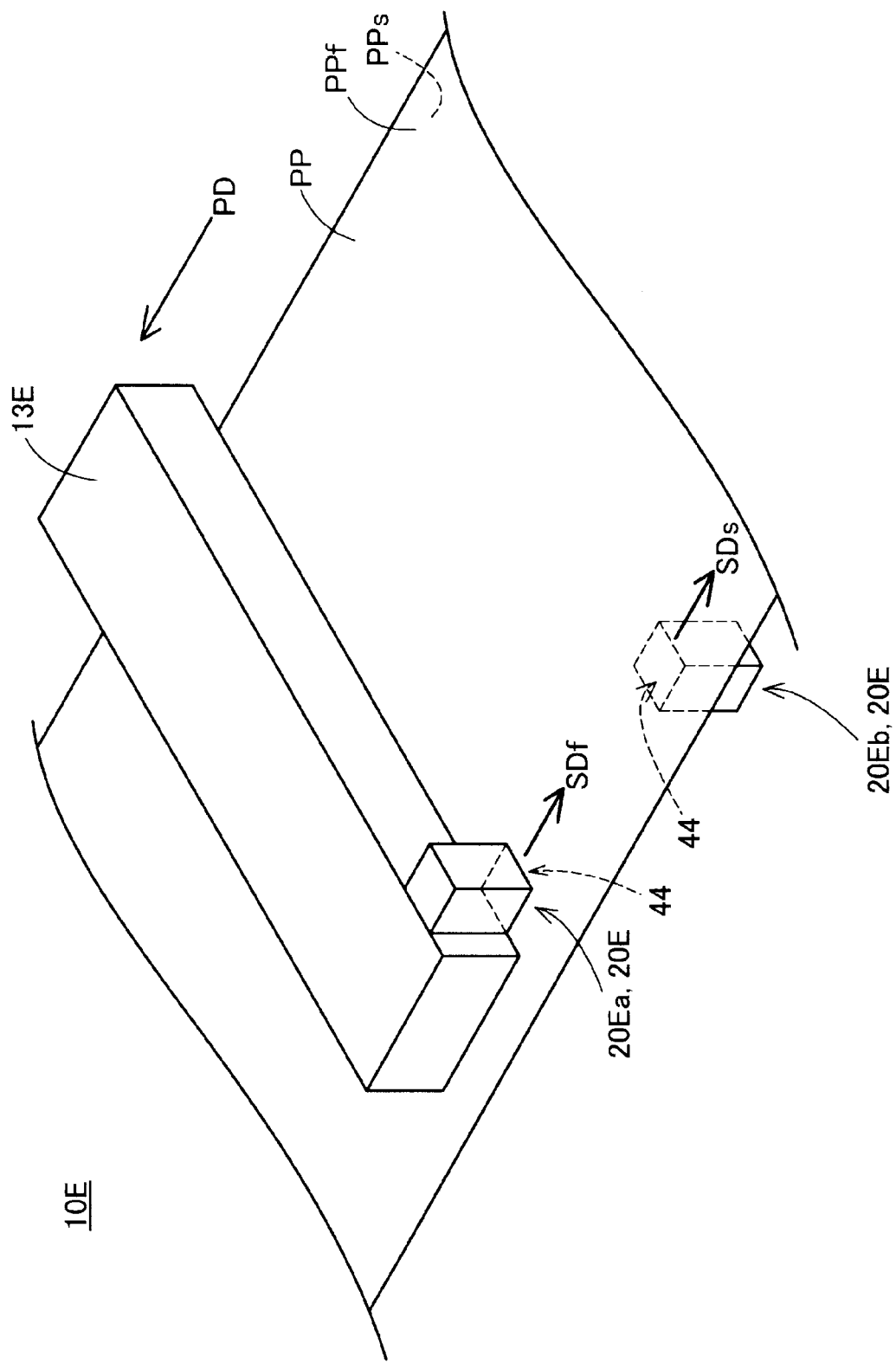

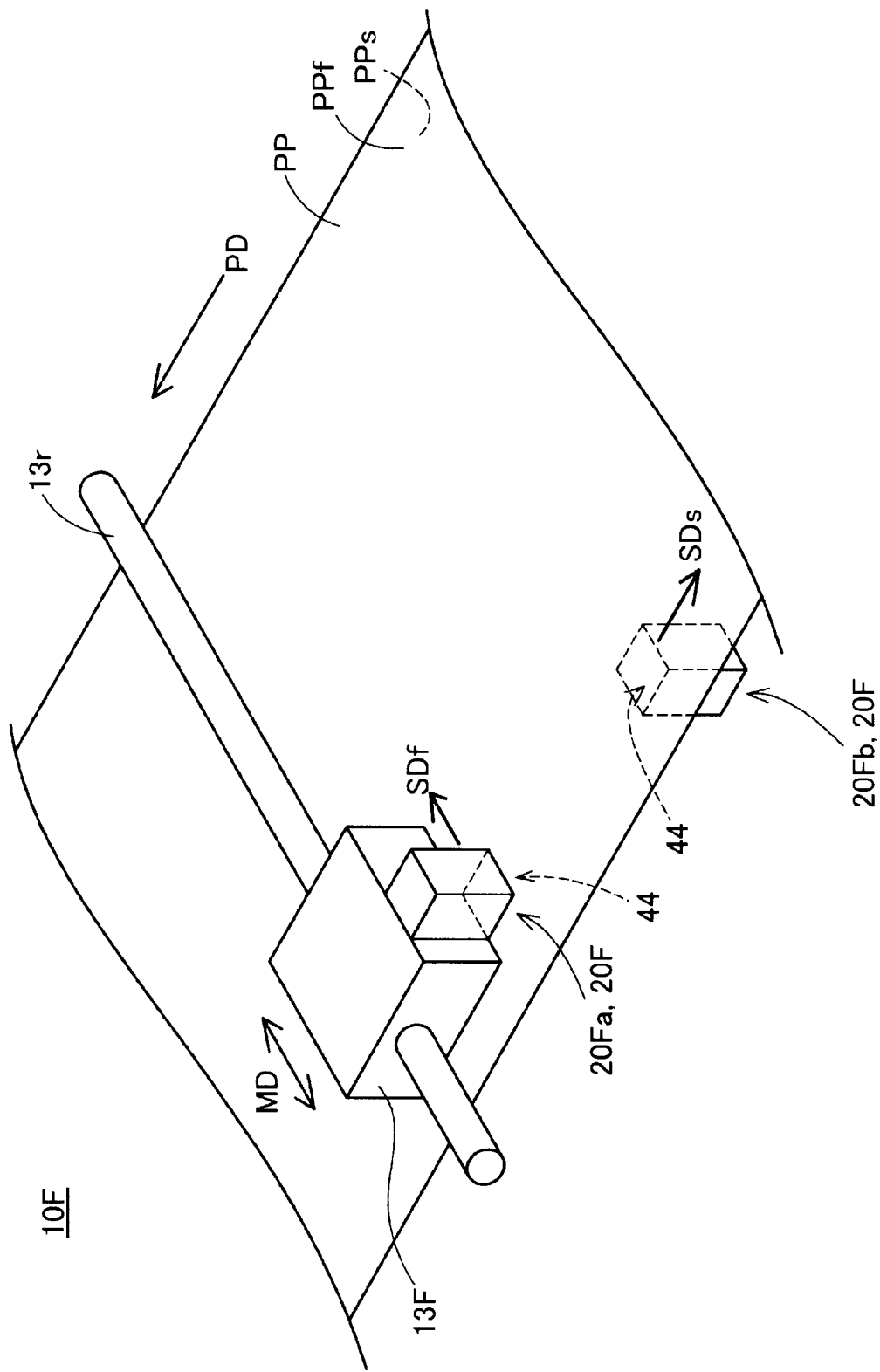

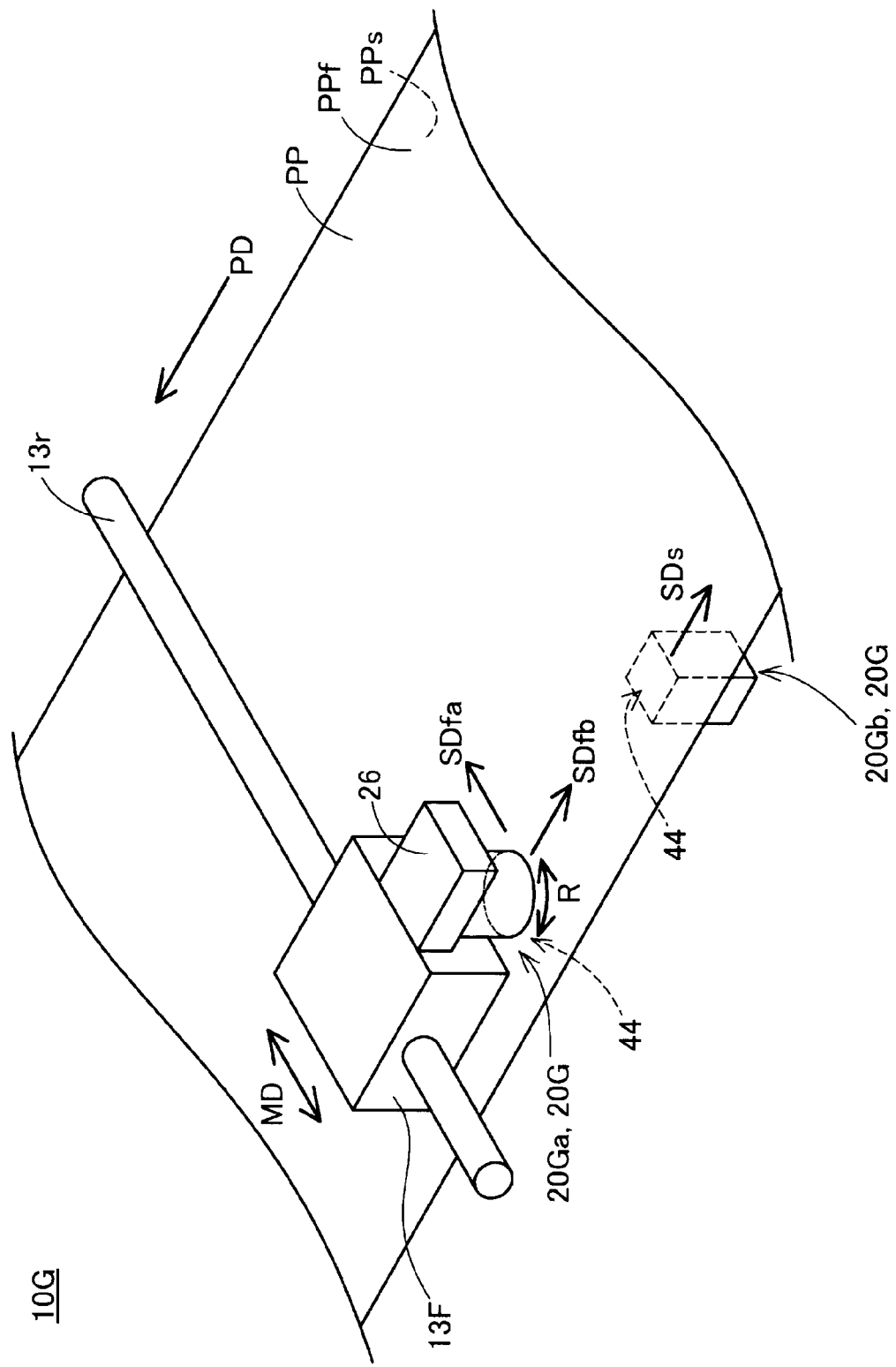

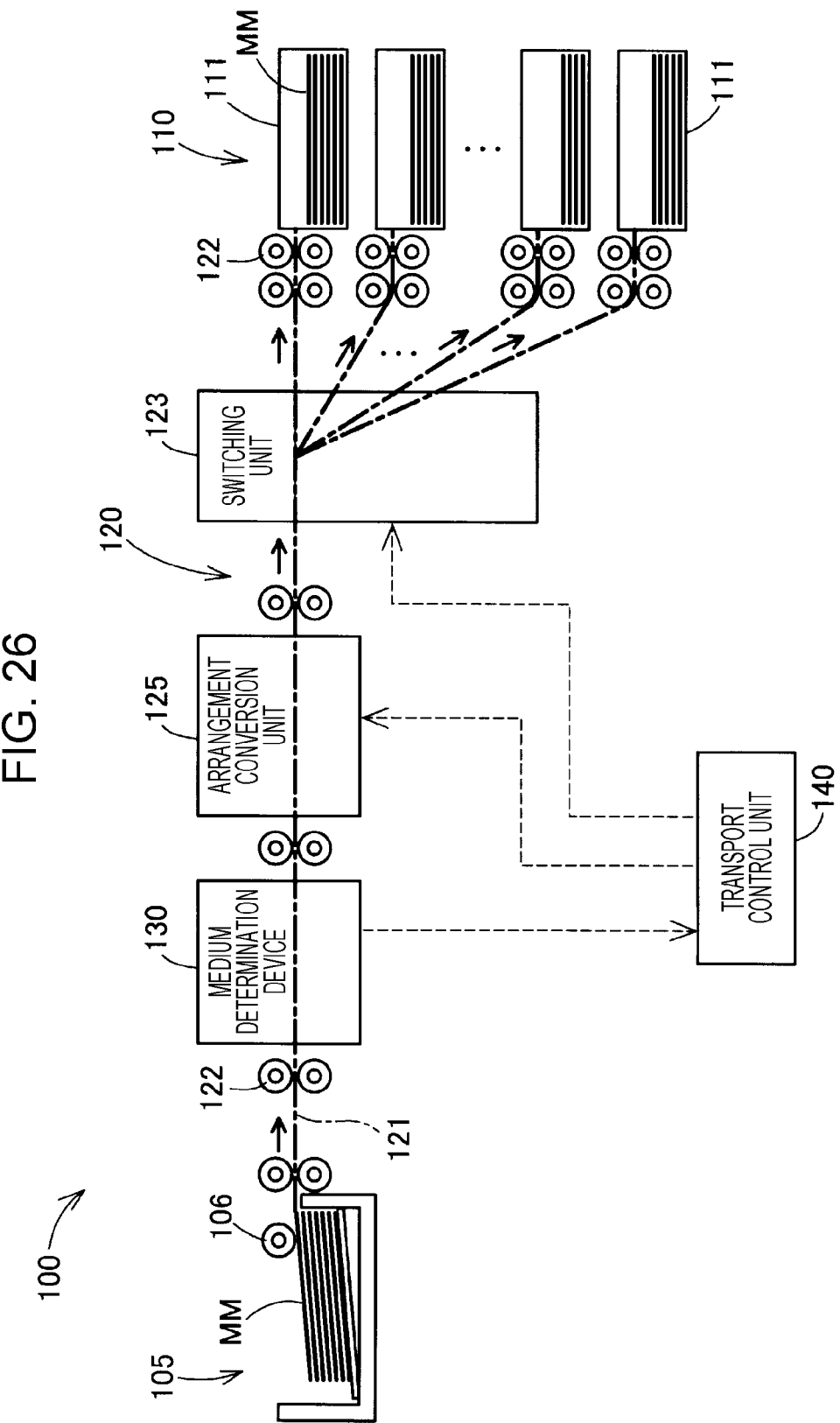

OPTICAL SCANNING DEVICE, TRANSPORT DEVICE, FEATURE DETECTION DEVICE, MEDIUM DETERMINATION DEVICE, SORTING DEVICE, AND MEDIUM SCANNING METHOD

CROSS-REFERENCE TO RELATED APPLICATIONS

The present application claims priority to Japanese Patent Application No. JP2016-061170, filed Mar. 25, 2016 and JP2016-240870, filed Dec. 13, 2016, which applications are hereby incorporated by reference in their entirety.

BACKGROUND

1. Technical Field

Embodiments of present invention relate to an optical scanning device, a transport device, a feature detection device, a medium determination device, a sorting device, and/or a medium scanning method.

2. Related Art

In general, a transport device transporting a printing paper is incorporated in an ink jet printer (referred to herein as a "printer"). A transport device may include a function of optically scanning a transport medium, which is being transported, with an optical scanning device in order to control the transport of the transport medium and a function of detecting parameters relating to a transport state of the transport medium such as a transport speed or a transport amount of the transport medium. Also, a transport device may include a feature detection device that detects a feature such as an uneven pattern in a surface of the transport medium by optically scanning the transport medium and that specifies a type of a medium. In the optical scanning device that performs the optical scanning, in general, an optical sensor technology, as described in, for example, JP-A-2007-303975, may be used. In this case, a light receiving element of the optical sensor, such as a photosensor, receives the reflected light of incoherent light beams emitted from a light emitting element.

In a spatial frequency sensitivity of an optical scanning device, in general, a plurality of notches where sensitivity sharply declines at a specific frequency (or small range of frequencies) are present. The presence of the notches indicates that there is a possibility that some pieces of information to be acquired by the optical scanning device at the specific frequency or frequencies are missing. However, until now, research on restraining the occurrence of a notch in the spatial frequency sensitivity of the optical scanning device has not been sufficiently conducted. This type of problem is not limited to the optical scanning device used in the transport device of the printer and is a common problem to be solved in a technical field of the optical sensor in which optical scanning is performed using the photosensor. At least, the problem is a common problem in a feature detection device that uses optical scanning to detect a feature of a medium, and in a determination device that uses optical scanning to determine a type of a medium, and in a sorting device that uses optical scanning to sort the media by a type.

SUMMARY

Embodiments of the invention can be realized in the following aspects.

(1) According to a first aspect of the invention, an optical scanning device is provided. The optical scanning device of the aspect may scan a medium using incoherent scanning light in a scanning direction. The optical scanning device of the aspect may include a scanning light emission unit, a reflected-light passing unit, a light-reception-signal output unit, and a signal generation unit. The scanning light emission unit may emit the scanning light. The reflected-light passing unit has a passing region through which a portion of reflected light, which is the scanning light reflected by the medium, passes. The light-reception-signal output unit may receive the reflected light passing through the passing region and output a signal representing a temporal change of intensity of the reflected light at a predetermined period. The signal generation unit may generate a frequency signal of each period at which a fast Fourier transform is performed on the signal output from the light-reception-signal output unit and output the frequency signal. An outer peripheral contour line of the passing region may include or be defined by a contour curve. The contour curve may be configured with a set of points where the coordinates in an orthogonal direction orthogonal to a scanning direction are uniquely determined with respect to the coordinates in the scanning direction and may render a curve protruded toward the passing region. When a region which is in contact with the contour curve in the passing region is divided into a plurality of quadrilateral minute regions of which areas are equivalent to one another and which extend from the contour curve to a predetermined coordinate position in the scanning direction and are continuously arranged in the orthogonal direction, widths of the minute regions in the scanning direction are different for each location in the orthogonal direction.

According to the optical scanning device of the aspect, the occurrence of the notch in the frequency signal generated in the signal generation unit is restrained. Accordingly, optical detection accuracy is increased in the optical scanning device.

(2) In the optical scanning device of one embodiment of the invention, when L is set as the coordinates in the scanning direction, x is set as the coordinates in the orthogonal direction, A and B are set as arbitrary positive numbers, C is set as an arbitrary real number, and $\alpha$ is set as an arbitrary negative number, a curve rendered by the contour curve may be represented as $$L = A \cdot (B \cdot x)^{\alpha} + C.$$

According to the optical scanning device of the aspect, occurrence of the notch in the frequency signal is further restrained.

(3) In the optical scanning device of one embodiment of the invention, when a is set as an arbitrary positive real number, the curve rendered by the contour curve may be represented as, $L = (2 \cdot x)^{-1/a}$.

According to the optical scanning device of the aspect, occurrence of the notch in the frequency signal is further restrained.

(4) In the optical scanning device of one embodiment of the invention the a may be a real number greater than or equal to 1 and less than or equal to 3.

According to the optical scanning device of the aspect, occurrence of the notch in the frequency signal is restrained and also a sharp decline in spatial frequency sensitivity to 0 is restrained.

(5) In the optical scanning device of one embodiment of the invention, the a may be 2.

According to the optical scanning device of one embodiment of the invention, it is possible to obtain a frequency signal having a shape approximating a quadratic curve.

(6) In the optical scanning device of one embodiment of the invention, the contour curve is a first contour curve and the outer peripheral contour line may further include a second contour curve which is located at a position opposing the first contour curve so as to sandwich the passing region in the scanning direction between the first and second contour curves. The second contour curve is in or has a mirror-symmetry with respect to the first contour curve in the scanning direction.

According to the optical scanning device of one embodiment of the invention, it is possible to increase an area of the passing region and increase a light receiving amount in the light-reception-signal output unit.

(7) In the optical scanning device of one embodiment of the invention the outer peripheral contour line may further include a third contour curve which is located at a position opposing the first contour curve so as to sandwich the passing region in the orthogonal direction and that is in a mirror-symmetry with respect to the first contour curve in the orthogonal direction. The outer peripheral contour line may include a fourth contour curve that is located at a position opposing the second contour curve so as to sandwich the passing region in the orthogonal direction and that is in or has a mirror-symmetry with respect to the second contour curve in the orthogonal direction.

According to the optical scanning device of one embodiment of the invention, it is possible to increase the area of the passing region.

(8) According to a second aspect of the invention, a transport device is provided. The transport device of the aspect may include a transport path, a first detection unit, a second detection unit, an operation unit, and a transport control unit. In the transport path, the transport medium may be transported in a transporting direction. The first detection unit and the second detection unit may be configured by any of the optical scanning devices of the aspect or embodiments described above that scan the transport medium by setting a direction along the transporting direction as a scanning direction. The operation unit may output a parameter relating to a transport state of the transport medium using a first frequency signal which is the frequency signal output from the signal generation unit of the first detection unit and a second frequency signal which is the frequency signal output from the signal generation unit of the second detection unit. The transport control unit may control the transport of the transport medium in the transport path using the parameter. A first detection point which is a position at which the first detection unit scans the transport medium and a second detection point which is a position at which the second detection unit scans the transport medium may be arranged with a predetermined separation distance in the transporting direction in the transport path. Thus, the first detection point and the second detection point may be separated by a predetermined separation distance. The operation unit may calculate the parameter using a period difference between a change in the first frequency signal and a change in the second frequency signal and the predetermined separation distance.

According to the transport device of one embodiment of the invention, the transport state of the transport medium can be more accurately detected and thus, transport accuracy of the transport medium is increased.

(9) According to a third aspect of the invention, a feature detection device is provided. The feature detection device of one embodiment of the invention may detect feature data that represents a surface feature of a medium. The feature detection device may include an optical scanning device and a feature data acquisition unit. The optical scanning device may be any of the optical scanning devices of the aspects or embodiments described above that scan the medium. The feature data acquisition unit may acquire a group of frequency signals generated at each period described above as the feature data.

According to the feature detection device of the aspect, the occurrence of a notch in the spatial frequency sensitivity is restrained in the optical scanning device and thus, it is possible to more accurately acquire the feature data of the medium.

(10) According to a fourth aspect of one embodiment of the invention, a medium determination device that determines a type of the medium is provided. The medium determination device of the aspect or embodiment may include a scanning unit that scans the medium, is configured with the optical scanning device of one or more of the aspects described above, and includes a first surface scanning unit and a second surface scanning unit that respectively scan a first surface and a second surface of the medium; a feature data acquisition unit that acquires a group of the frequency signals generated by the first surface scanning unit at each period described above as first surface feature data and that acquires a group of the frequency signals generated by the second surface scanning unit at each period described above as second surface feature data; a master data storing unit that stores master data prepared for each type of the medium in advance and including first surface collation data corresponding to the first surface feature data and second surface collation data corresponding to the second surface feature data; and a determination processing unit that determines the type of the medium by executing first surface collation processing of collating the first surface feature data and the first surface collation data and executing second surface collation processing of collating the second surface feature data and the second surface collation data.

According to the medium determination device of the aspect, the frequency signal acquired using the optical scanning device of the aspect is used and thus, a determination accuracy of the type of the medium is increased. Two pieces of feature data acquired from each of a first surface and a second surface of the medium (e.g., one or more pieces of feature data from each surface) are used in the determination of the type of the medium and thus, the determination accuracy of the type of the medium is further increased.

(11) In the medium determination device of one embodiment of the invention, the first surface scanning unit scans the first surface of the medium in a first direction and a second direction intersecting with the first direction; the first surface feature data acquired by the feature data acquisition unit includes first feature data generated when the first surface scanning unit scans the medium in the first direction and second feature data generated when the first surface scanning unit scans the medium in the second direction; the first surface collation data stored by the master data storing unit includes first collation data corresponding to the first feature data and second collation data corresponding to the second feature data; and the determination processing unit may collate the first feature data with the first collation data and collate the second feature data with the second collation data in first surface collation processing.

According to the medium determination device of the aspect, the first surface is scanned in at least two directions to detect a feature of a medium and thus, the determination accuracy of the type of the medium is further increased.

(12) In the medium determination device of one embodiment of the invention, the second surface scanning unit scans the second surface of the medium in a third direction and a fourth direction intersecting with the third direction; the second surface feature data acquired by the feature data acquisition unit includes third feature data generated when the second surface scanning unit scans the medium in the third direction and fourth feature data generated when the second surface scanning unit scans the medium in the fourth direction; the second surface collation data stored by the master data storing unit includes third collation data corresponding to the third feature data and fourth collation data corresponding to the fourth feature data; and the determination processing unit may collate the third feature data with the third collation data and collate the fourth feature data with the fourth collation data in second surface collation processing.

According to the medium determination device of the aspect, the second surface is scanned in at least two directions to detect a feature of a medium and thus, the determination accuracy of the type of the medium is further increased.

(13) According to a fifth aspect of embodiments of the invention, a medium determination device that determines a type of a medium is provided. The medium determination device of the aspect may include a scanning unit that is configured with the optical scanning device of one or more of the aspects described above, scans the medium, and includes a first direction scanning unit scanning the medium in a first scanning direction and a second direction scanning unit scanning the medium in a second scanning direction intersecting with the first scanning direction; a feature data acquisition unit that acquires a group of the frequency signals generated by the first direction scanning unit at each period described above as first direction feature data and that acquires a group of the frequency signals generated by the second direction scanning unit at each period described above as second direction feature data; a master data storing unit that stores master data prepared for each type of the medium in advance and including first direction collation data corresponding to the first direction feature data and second direction collation data corresponding to the second direction feature data; and a determination processing unit that determines the type of the medium by executing collation processing of collating the first direction feature data with the first direction collation data and collating the second direction feature data with the second direction collation data.

According to the medium determination device of the aspect, the frequency signal acquired using the optical scanning device of the aspects described above is used and thus, the determination accuracy of the type of the medium is improved. Two pieces of feature data acquired by scanning in at least two directions are used in the determination of the type of the medium and thus, the determination accuracy of the type of the medium is further improved.

(14) According to a sixth aspect of one embodiment of the invention, a sorting device that sorts the media by each type is provided. The sorting device includes a plurality of storing units that each stores the medium by a type; a transport unit that includes a transport path through which the medium is transported and a switching unit switching a connection destination of the transport path to any of the plurality of storing units; a medium determination device that is described in one or more of the aspects described above and that determines the type of the medium transported by the transport unit; and a transport control unit that controls the switching unit according to a determination result of the medium determination device and that switches a transport destination of the medium. The transport destination is selected based on the determination result.

According to the sorting device of the aspect, the media may be sorted by each type of the medium using the medium determination device which uses the optical scanning device of the aspects described above. Thus, accuracy of the sorting is improved.

(15) According to a seventh aspect of embodiments of the invention, a method for scanning a medium is provided. The method may include scanning a medium by emitting incoherent scanning light to the medium in a predetermined scanning direction; causing a portion of reflected light, which is scanning light reflected by the medium, to pass through a passing region; receiving the reflected light passing through the passing region and outputting a signal representing a temporal change of an intensity of the reflected light at a predetermined period; and generating a frequency signal of each period at which the fast Fourier transform is performed on the signal and outputting the frequency signal. An outer peripheral contour line of the passing region includes a contour curve configured with a set of points where the coordinates in an orthogonal direction orthogonal to a scanning direction are uniquely determined with respect to the coordinates in the scanning direction. The contour curve renders a curve protruded toward the passing region, and when a region which is in contact with the contour curve in the passing region is divided into a plurality of quadrilateral minute regions of which areas are equivalent to one another and which extend from the contour curve to a predetermined coordinate position in the scanning direction and are continuously arranged in the orthogonal direction, widths of the minute regions in the scanning direction are different for each location in the orthogonal direction.

A plurality of constitutional elements included in respective aspects and embodiments of the invention described above are not necessarily essential constituents and some constitutional elements of the plurality of constitutional elements can be appropriately modified, deleted, or replaced with new constitutional elements, or partial deletion of limitation contents of the constitutional elements may be made in order to solve some or all of the problems described above or achieve some or all of the effects described in the specification. Some or all of the technical features included in an aspect or embodiments of the invention described above may be combined with some or all of the technical features included in other aspects of the invention described above to thereby make it possible to regard the combination as an independent aspect or embodiment of the invention in order to solve some or all of the problems described above or to achieve some or all of the effects described in the specification.

Embodiments of the invention may also be realized by various aspects other than the optical scanning device, the transport device, and the feature detection device. For example, embodiments of the invention may also be realized as an apparatus that detects a feature or a speed of a target, which is relatively moved (e.g., when the target is transported), using a photosensor. Embodiments of the invention may also b include a control method of the apparatus, the optical scanning device, the transport device, the feature detection device or the like described above, a computer program for realizing the control method, a non-transitory recording medium having the computer program or the like recorded therein. In addition, embodiments of the invention may also be realized by an aspect or embodiment having a mask member for specifying a cross-sectional shape of reflected light reflected from a medium, a shape of a passing region through which reflected light passes or the like as a characteristic of configuration.

BRIEF DESCRIPTION OF THE DRAWINGS

Embodiments of the invention will be described with reference to the accompanying drawings, wherein like numbers reference like elements.

FIG. 18A is a diagram illustrating an arrangement configuration of two scanning units of the fifth embodiment.

FIG. 20A is a perspective view schematically illustrating a region including a scanning unit of a printing apparatus in a sixth embodiment.

FIG. 22A is a perspective view schematically illustrating a region including a scanning unit of a printing apparatus in a seventh embodiment.

FIG. 26 is a schematic diagram illustrating a configuration of a sorting device in the eleventh embodiment.

DESCRIPTION OF EXEMPLARY EMBODIMENTS

First Embodiment

Figure 1:
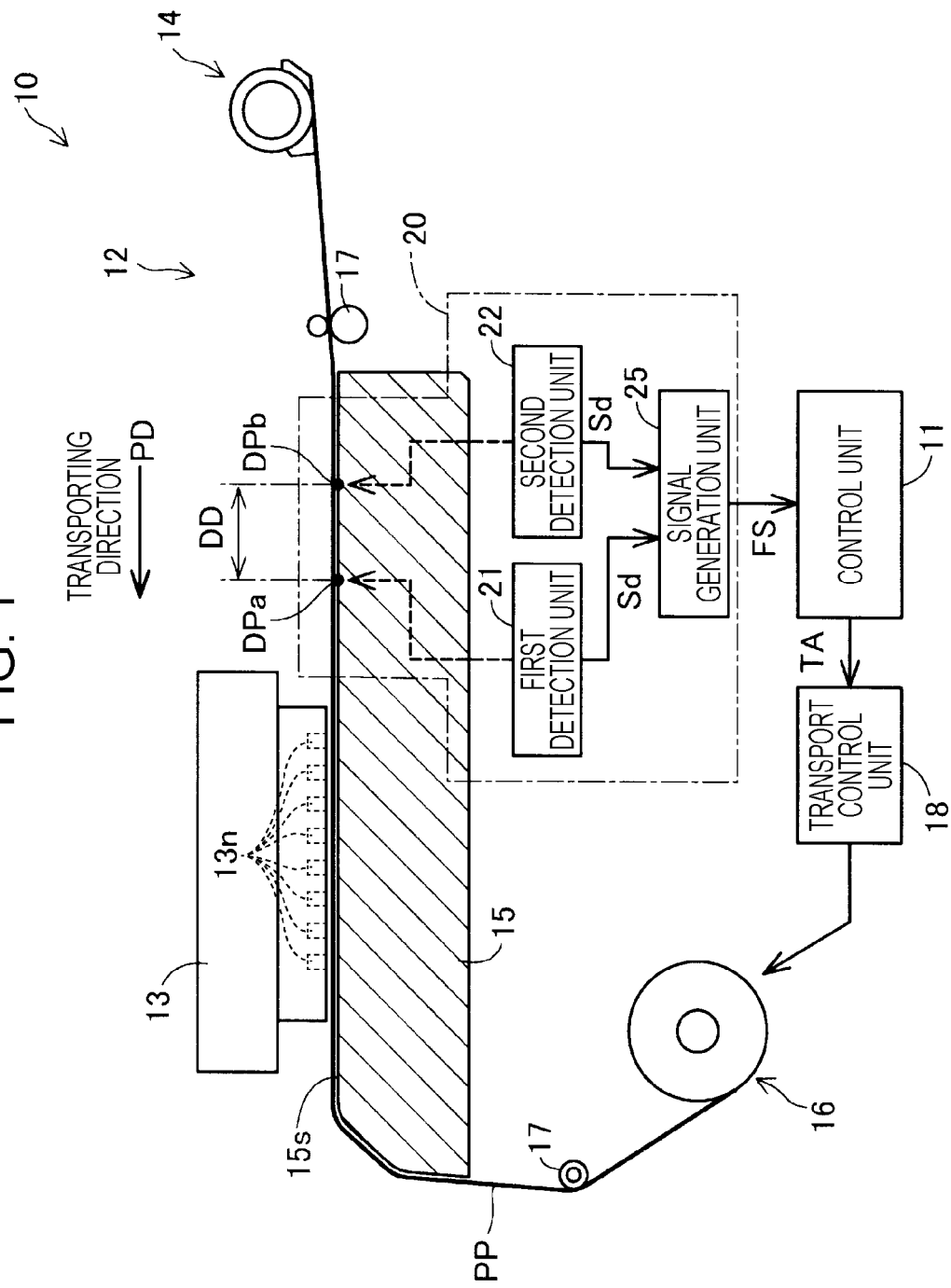
FIG. 1 is a schematic diagram illustrating an example configuration of a printing apparatus.

FIG. 1 is a schematic diagram illustrating a configuration of a printing apparatus 10 that includes an optical scanning device and a transport device of a first embodiment of the invention. The printing apparatus 10 may be an ink jet printer that ejects ink (or an apparatus that ejects a different liquid) onto a printing paper PP (or other medium), which is an example of a printing medium, to form an image. The printing apparatus 10 includes a control unit 11, a transport device 12, a printing head unit 13, and an optical scanning device 20.

The control unit 11 may include a microcomputer including a central processing unit (CPU) and a main storage device (RAM), and exhibits or performs various functions by allowing the CPU to read various instructions or programs from the RAM and execute the instructions or programs. The control unit 11 functions as a control unit of the printing apparatus 10. The control unit 11 mainly controls the transport of the printing paper PP by the transport device 12 and the ejection of inks in the printing head unit 13 according to printing data input from the outside of the printing apparatus 10 or a user's manipulation received through a manipulation unit (not illustrated) of the printing apparatus 10. In the first embodiment, the control unit 11 also functions as an operation unit of the transport device 12 that interprets a frequency signal output from the optical scanning device 20 of the first embodiment and outputs a parameter relating to a transport state of the printing paper PP (which will be described later). In the first embodiment, the parameter relating to the transport state of the printing paper PP is a transport amount (moving distance) of the printing paper PP.

In one embodiment, the transport device 12 transports a strip-shaped printing paper PP in a longitudinal direction of the transport device 12 as a transport medium under the control of the control unit 11. The transport device 12 includes a delivery unit 14, a support base 15, a winding unit 16, a plurality of transport rollers 17, a transport control unit 18, and an optical scanning device 20. The delivery unit 14 releases the printing paper PP from a state of being wound in a roll shape to be delivered. The printing paper PP delivered from the delivery unit 14 is transported on a base surface 15s of the support base 15 while tension is applied to the printing paper PP by the transport roller 17 or by multiple transport rollers 17.

The printing paper PP is transported along the base surface 15s in the state of facing the base surface 15s of the support base 15. In FIG. 1, a transporting direction PD of the printing paper PP on the base surface 15s is illustrated by an arrow. The base surface 15s corresponds to a subordinate concept of a transport path in the invention. In the first embodiment, a surface of the medium facing upward, which is opposite to the base surface 15s side of the printing paper PP facing the base surface 15s side, is a printing surface. Thus, one side or surface of the medium faces the base surface 15s and the opposite side or surface of the medium is surface on which an image is formed. A transport roller (not illustrated) assisting the transport of the printing paper PP may also be provided in the support base 15.

The winding unit 16 is provided on the downstream side of the support base 15 and winds the printing paper PP transported along an upper surface of the base surface 15s in a roll shape by a rotation driving force of a motor (not illustrated). Tension is applied to the printing paper PP between the winding unit 16 and the support base 15 by the transport roller 17. The transport control unit 18 controls a rotation driving of a motor of the winding unit 16 using a transport amount of the printing paper PP acquired from the control unit 11 and controls the transport of the printing paper PP on the base surface 15s. Thus, the motor may be driven to rotate the winding unit based on the transport amount of the printing paper PP.

In one embodiment, the optical scanning device 20 irradiates scanning light toward a surface (e.g., a rear surface) of the paper PP opposite to the printing surface of the printing paper PP to scan the printing paper PP and receives reflected light of the scanning light. In other words, at least some of the scanning light reflected by the medium is received by the optical scanning device 20. The optical scanning device 20 may include a first detection unit 21, a second detection unit 22, and a signal generation unit 25.

The first detection unit 21 and the second detection unit 22 have the same configuration in one example and emit scanning light to scan the rear surface of the printing paper PP, respectively. In the first embodiment, a first detection point DPa at which the first detection unit 21 scans the printing paper PP and a second detection point DPb at which the second detection unit 22 scans the printing paper PP are provided in a region of the upstream side of the base surface 15s. The first detection point DPa and the second detection point DPb are arranged in one line, in one example, and are separated from each other by a predetermined separation distance in a transporting direction of the printing paper PP. Details of the configuration of the first detection unit 21 and the second detection unit 22 will be described later.

The signal generation unit 25 acquires light reception signals Sd representing scanning results of the first detection unit 21 and the second detection unit 22 from the first detection unit 21 and the second detection unit. The signal generation unit 25 performs a fast Fourier transform (FFT) on each of the light reception signals Sd to thereby generate a frequency signal FS. The frequency signal FS is output to the control unit 11. The control unit 11 calculates a transport amount TA which is a parameter representing a transport state of the printing paper PP using the frequency signal FS. Processing for calculating the light reception signal Sd, the frequency signal FS, and the transport amount TA of the printing paper PP by the control unit 11 will be described later.

The printing head unit 13 is provided at a position opposing the printing surface of the printing paper PP which is transported on the base surface 15s of the support base 15. The printing head unit 13 is positioned on the downstream side of both the first detection point DPa and the second detection point DPb. The printing head unit 13 includes a plurality of nozzles 13n, ejects ink drops from each nozzle 13n under control of the control unit 11, and forms a printing image by recording ink dots onto the printing surface of the printing paper PP. In a region of the support base 15 facing the printing head unit 13, a suction unit that sucks or draws the printing paper PP onto the base surface 15s by a suction force of a suction pump is provided.

Figure 2:
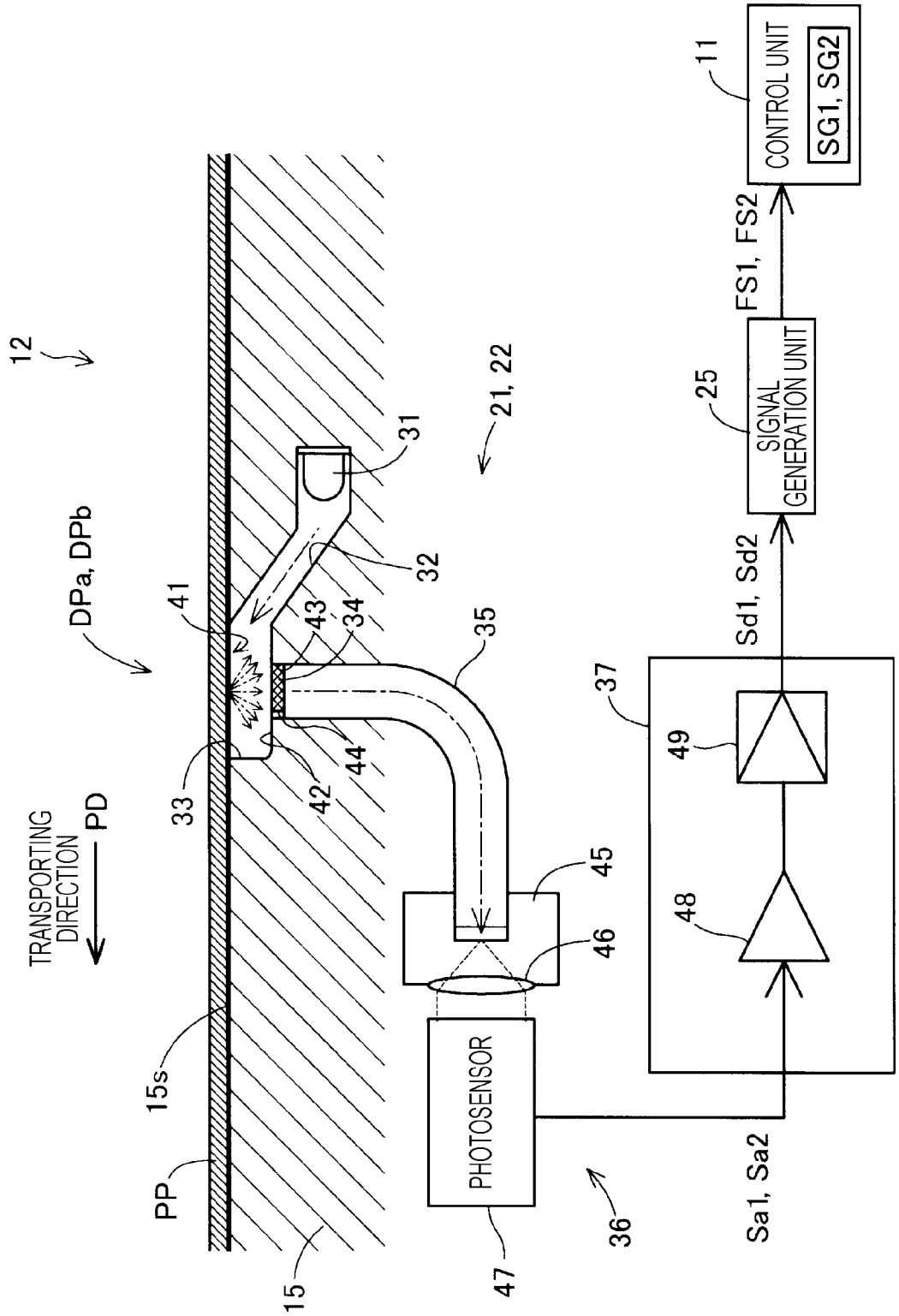
FIG. 2 is a schematic diagram illustrating a configuration of a first detection unit and a second detection unit.

FIG. 2 is a schematic diagram illustrating a configuration of the first detection unit 21 and the second detection unit 22. As described above, the first detection unit 21 and the second detection unit 22 have the same configuration except that detection positions on the transport path of the printing paper PP are different. In one embodiment, the first detection unit 21 and the second detection unit 22 are positioned at different locations in the transport path. One of the detection units may be positioned more upstream than the other. The first and second detection units may be separated from each other in the transport direction and/or in a direction transverse to the transport direction. Unless otherwise stated, the following description of the configuration of the first detection unit 21 is also a description of the configuration of the second detection unit 22. The first detection unit 21 includes a light emitting element 31, a light guide unit 32, a reflection unit 33, a mask member 34, an optical fiber 35 (or other light pipe or guide), a light receiving sensor unit 36, and a light receiving circuit 37.

The light emitting element 31 emits scanning light. The light emitting element 31 emits, for example, incoherent light whose wavelength is in the infrared range as scanning light. In the first embodiment, the light emitting element 31 may include an LED. The light emitting element 31 corresponds to a subordinate concept of a scanning light emission unit in embodiments of the invention. In the first embodiment, the light emitting element 31 is fixed inside the support base 15. The light guide unit 32 is a passage which guides the scanning light emitted from the light emitting element 31 to the reflection unit 33. The scanning light is repeatedly reflected on an inner wall surface of the light guide unit 32 and arrives on or at the reflection unit 33. In the first embodiment, the light guide unit 32 is provided inside the support base 15. The light guide unit 32 may also be configured by an optical fiber.

The reflection unit 33 is a portion that reflects or guides the scanning light emitted from the light guide unit 32 onto the rear surface of the printing paper PP (e.g., through a transparent window in the surface of the support base or through open space). A formation position of the reflection unit 33 of the first detection unit 21 is a position of a first detection point DPa described above. Similarly, a formation position of the reflection unit 33 of the second detection unit 22 is a position of a second detection point DPb. In the first embodiment, the reflection unit 33 is formed as a recessed space of the support base 15 which opens upward on the base surface 15s. The printing paper PP is transported on or over the reflection unit 33 in a state where an opening 41 of the reflection unit 33 is closed; however the scanning light reaches the rear surface of the printing paper PP. The light guide unit 32 is connected to the reflection unit 33 from obliquely below and the scanning light guided by the light guide unit 32 is irradiated toward the rear surface of the printing paper PP being transported through the opening 41. The position at which the printing paper PP is irradiated with the scanning light is relatively changed due to a displacement of the printing paper PP being transported. In other words, the position at which the medium is scanned changes as the medium is transported. The rear surface of the printing paper PP is scanned by the scanning light emitted from the light emitting element 31 in a direction, which is opposite to the transporting direction PD of the printing paper PP and is set as the scanning direction, in the reflection unit 33.

An opening portion 43 is provided on the bottom wall surface 42 of the reflection unit 33. One end of the optical fiber 35 is connected to the opening portion 43 and the other end is connected to the light receiving sensor unit 36. A portion of diffused and reflected light (in the following, simply referred to as "reflected light") that is the scanning light reflected by the printing paper PP passes through an opening region of the opening portion 43 and is guided to the light receiving sensor unit 36 through the optical fiber 35. The remaining portion of reflected light that does not pass through the opening region of the opening portion 43 into the optical fiber 35 is shielded.

In one embodiment, a mask member 34 is attached to the opening portion 43. The mask member 34 may be a plate-shaped member for specifying or defining an opening shape of the opening portion 43 and is attached to close a portion of the opening region of the opening portion 43. The opening region in a mask opening 44 corresponds to a subordinate concept of the passing region and the opening portion 43 corresponds to a subordinate concept of a reflected-light passing unit in the invention. The opening shape of the mask opening 44 will be described later. The mask member 34 may not be configured by a plate-shaped member. The mask member 34 may be configured by another member capable of shielding a portion of the opening region of the opening portion 43 from light. For example, the mask member 34 may be configured by a fibrous member. The mask member 34 may be configured by a member in which a shape of an opening region, through which light passes, is specified by a surface treatment such as a coating.

The light receiving sensor unit 36 includes a connector portion 45, a lens 46, and a photosensor 47. The connector portion 45 may be a resin member, holds the other end of the optical fiber 35, and guides reflected light emitted from the optical fiber 35 to the lens 46 without allowing the emitted light (e.g., the reflected light transmitted through the optical fiber) to leak. The lens 46 is fixedly attached to the connector portion 45 and condenses the reflected light incident onto the lens 46 to a light receiving portion of the photosensor 47. The photosensor 47 may include, for example, a photodiode. The photosensor 47 converts the received light into an analog electrical signal (in the following, referred to as a "light reception signal Sa") representing an intensity of the received light and outputs the light reception signal Sa to the light receiving circuit 37.

The light receiving circuit 37 includes an amplifier 48 and an AD (analog-digital) converter 49. The amplifier 48 amplifies the light reception signal Sa output from the photosensor 47 so as to be fit to an input range of the AD converter 49. The AD converter 49 quantizes the light reception signal Sa, which is an analog signal, in order at a predetermined sampling period based on a sampling signal supplied from the signal generation unit 25, converts the light reception signal Sa into a light reception signal Sd, which is a digital signal, at each sampling period, and outputs the light reception signal Sd to the signal generation unit 25. The light reception signal Sd, which is a digital signal, can be interpreted as a signal that represents a temporal change in intensity of emitted light which is output at a predetermined period. The first detection unit 21 and the second detection unit 22 correspond to a subordinate concept of the light-reception-signal output unit in embodiments of the invention and the signal generation unit 25 corresponds to a subordinate concept of the signal generation unit in embodiments of the invention.

A first light reception signal Sa1 is output, as the light reception signal Sa which is an analog signal, from the photosensor 47 of the first detection unit 21. A first light reception signal Sd1 is output, as the light reception signal Sd which is a digital signal, from the light receiving circuit 37 of the first detection unit 21. On the other hand, a second light reception signal Sa2 is output, as the light reception signal Sa which is an analog signal, from the photosensor 47 of the second detection unit 22. A second light reception signal Sd2 is output, as the light reception signal Sd which is a digital signal, from the light receiving circuit 37 of the second detection unit 22.

The signal generation unit 25 performs the FFT on each of the light reception signals Sd1 and Sd2 output at each sampling period as described above and generates a frequency signal FS. Specifically, the signal generation unit 25 generates a first frequency signal FS1 from the first light reception signal Sd1 and generates a second frequency signal FS2 from the second light reception signal Sd2. The frequency signal FS obtained in the optical scanning device 20 of the first embodiment will be described later.

The control unit 11 corrects the first frequency signal FS1 and the second frequency signal FS2 output from the signal generation unit 25 at each sampling period by or using a quadratic function (which may be predetermined), respectively, and stores pieces of corrected data in a storage device (not illustrated) in a time-series of generation. In the following, a group of pieces of time-series data generated from the first frequency signal FS1 and stored in the storage device is referred to as a "first signal group SG1" and a group of pieces of time-series data generated from the second frequency signal FS2 and stored in the storage device is referred to as a "second signal group SG2".

Figure 3:
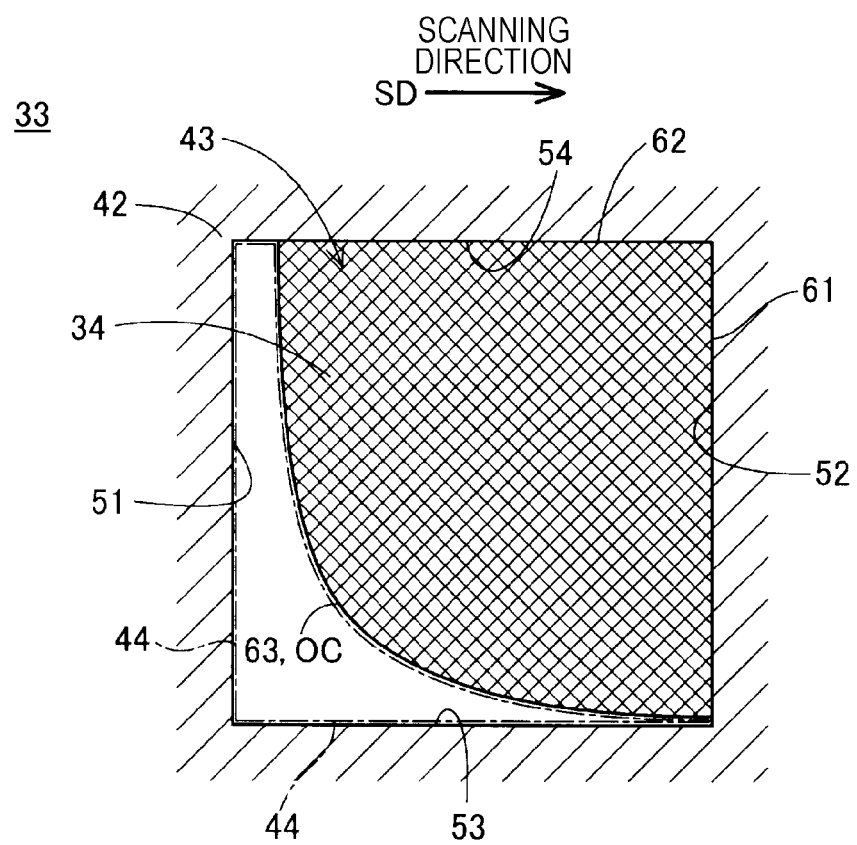
FIG. 3 is a schematic diagram that illustrates and describes an opening shape of a mask opening.

FIG. 3 is a schematic diagram for describing an opening shape of the mask opening 44 through which the reflected light passes in the reflection unit 33. In FIG. 3, the opening portion 43 when viewed directly opposite to the bottom wall surface 42 of the reflection unit 33 is illustrated. In FIG. 3, an arrow indicating the scanning direction SD along which the printing paper PP is scanned by the scanning light is illustrated.

In the first embodiment, the opening portion 43 has a substantially quadrilateral opening shape surrounded by four linear side portions 51 to 54. The first side portion 51 and the second side portion 52 are respectively orthogonal to the scanning direction SD and are located at positions facing each other in the scanning direction SD. In the scanning direction, the first side portion 51 is positioned at the upstream side and the second side portion 52 is positioned at the downstream side. The third side portion 53 and the fourth side portion 54 are in parallel to the scanning direction SD and face each other so as to sandwich the first side portion 51 and the second side portion 52.

As described above, the mask member 34 which closes a portion of the opening region of the opening portion 43 and specifies an opening shape is disposed in the opening portion 43. The mask member 34 includes a first end portion 61, a second end portion 62, and a third end portion 63 that configure an outer peripheral contour line of the mask member 34. The first end portion 61 is a linear portion disposed in close contact with the second side portion 52 of the opening portion 43. A length of the first end portion 61 is slightly shorter than that of the second side portion 52. The second end portion 62 is a linear portion disposed in close contact with the fourth side portion 54 of the opening portion 43. A length of the second end portion 62 is slightly shorter than that of the fourth side portion 54. A corner portion where the first end portion 61 and the second end portion 62 intersect each other is disposed so as to be fit into a corner portion between the second side portion 52 and the fourth side portion 54 of the opening portion 43. A spacing of a clearance formed between the first end portion 61 and the third side portion 53 is smaller than that formed between the second end portion 62 and the first side portion 51.

The third end portion 63 is a curved line portion intersecting with the first end portion 61 and the second end portion 62. The third end portion 63 extends from a position close to the first side portion 51 in the fourth side portion 54 while rendering a curve which is gently curved toward the third side portion 53 along the first side portion 51. The curvature of the curve at a position close to the third side portion 53 becomes large, and the curve is curved in a direction toward the second side portion 52, reaches a position in the vicinity of a corner portion between the second side portion 52 and the third side portion 53 while rendering a curve which is gently curved along the third side portion 53, and intersects with the second end portion 62.

As described above, the mask member 34 is fitted into a portion of the opening portion 43 such that the mask opening 44 is formed on the bottom wall surface 42. The outer peripheral contour line surrounding the mask opening 44 includes a contour curve OC configured by the third end portion 63 of the mask member 34. The contour curve OC renders a curve protruded toward an opening region of the mask opening 44. The contour curve OC may be interpreted as a curve configured with a set of points where the coordinates in an orthogonal direction orthogonal to the scanning direction SD are uniquely determined with respect to the coordinates in the scanning direction SD. The contour curve OC corresponds to a subordinate concept of the contour curve in embodiments of the invention. In the first embodiment, the contour curve OC approximates a curve represented by a functional expression, but details of the contour curve OC will be described later. According to the optical scanning device 20 of the first embodiment, the reflected light is received through the mask opening 44 having the contour curve described above to thereby make it possible to obtain the frequency signal FS to be described in the following.

Figure 4:
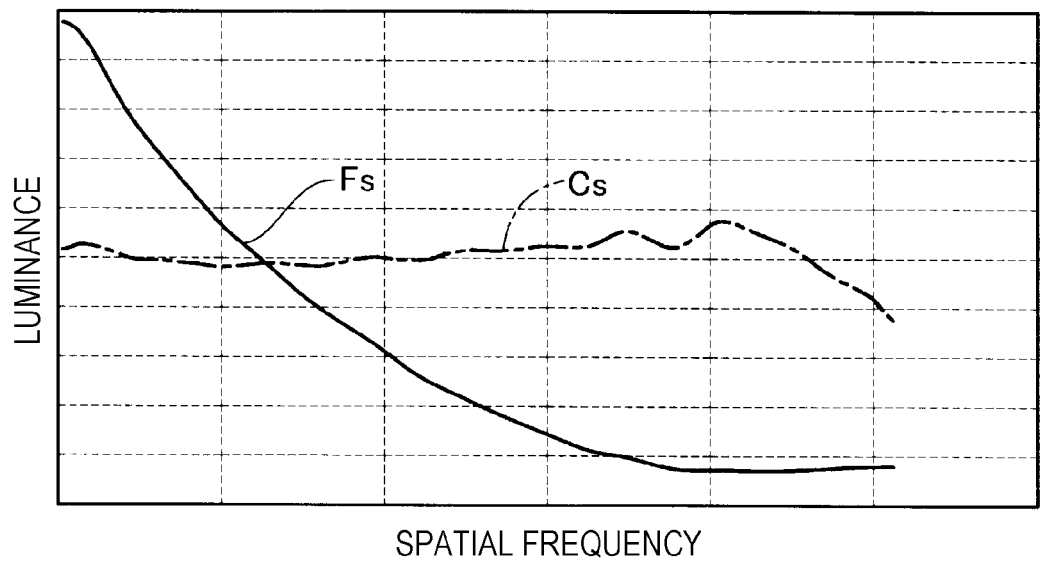
FIG. 4 is a graph illustrating an example of a frequency signal acquired by a control unit.

FIG. 4 is a graph illustrating an example of the frequency signal FS acquired from the signal generation unit 25 of the optical scanning device 20 by the control unit 11. The frequency signal FS output by the signal generation unit 25 of the optical scanning device 20 is represented by a graph where the vertical axis is set as luminance and the horizontal axis is set as a spatial frequency.

The frequency signal FS is a signal that varies according to an appearance configuration, material of a printing paper PP, or an internal structure in a region of the printing paper PP existing within or corresponding to the mask opening 44 when the printing paper PP is irradiated with the scanning light, and a signal that represents features detected from the rear surface side of the printing paper PP in the region. In the "appearance configuration", for example, surface properties such as a minute uneven pattern or patterns existing on the surface of the printing paper PP or a color pattern or patterns are included. According to the optical scanning device 20 of the first embodiment, the frequency signal FS is obtained as a signal which renders a curve graph approximating a quadratic curve where the luminance is gradually decreased as the spatial frequency is increased. As such, according to the optical scanning device 20 of the first embodiment, the appearance of a notch, which will be described next using FIG. 5 to FIG. 7, in the frequency signal FS is restrained.

Figure 5:
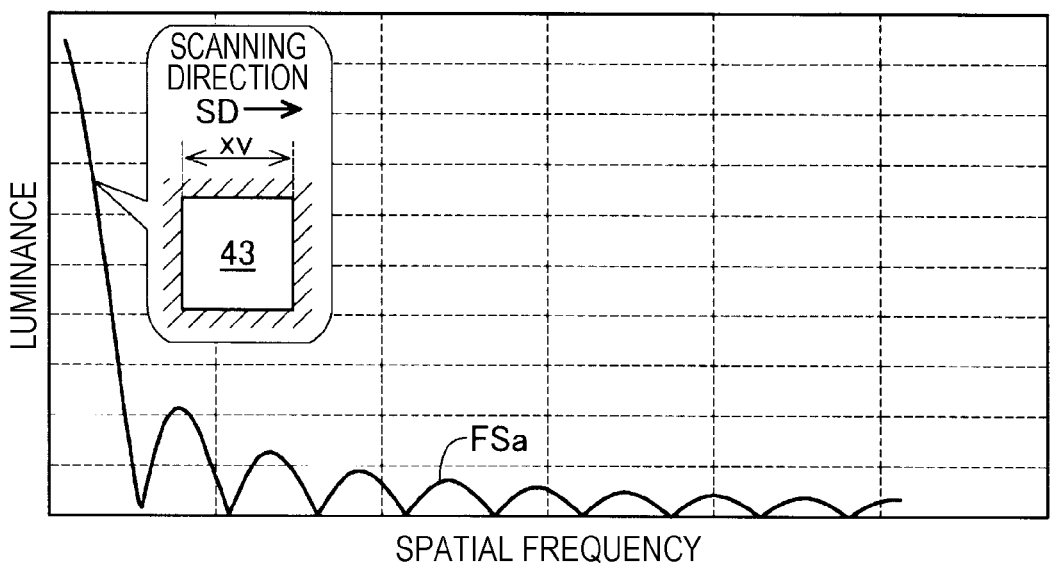
FIG. 5 is a graph illustrating an example of a frequency signal acquired in an optical scanning device of a first comparative example.

FIG. 5 is a graph illustrating a first comparative example of a frequency signal FSa acquired in an optical scanning device that has almost the same configuration as that of the optical scanning device 20 of the first embodiment except that the mask member 34 is omitted in the opening portion 43 of the reflection unit 33. The example of FIG. 5 is obtained when the same medium as that, which is used when the frequency signal FS described with reference to FIG. 4 is obtained, is used as a scanning target.

In the optical scanning device of the first comparative example, the photosensor receives the reflected light passing through the entirety of the opening region, which has a substantially quadrilateral shape, of the opening portion 43. That is, in a field of view of the photosensor, as illustrated in a balloon of FIG. 5, an opening width xv which is a width of the opening region in the scanning direction SD is almost constant in the orthogonal direction orthogonal to the scanning direction. In the frequency signal FSa acquired in the configuration described above, occurrence of the notch in which the luminance is declined to 0 in the spatial frequency sensitivity is periodically repeated.

Figure 6:
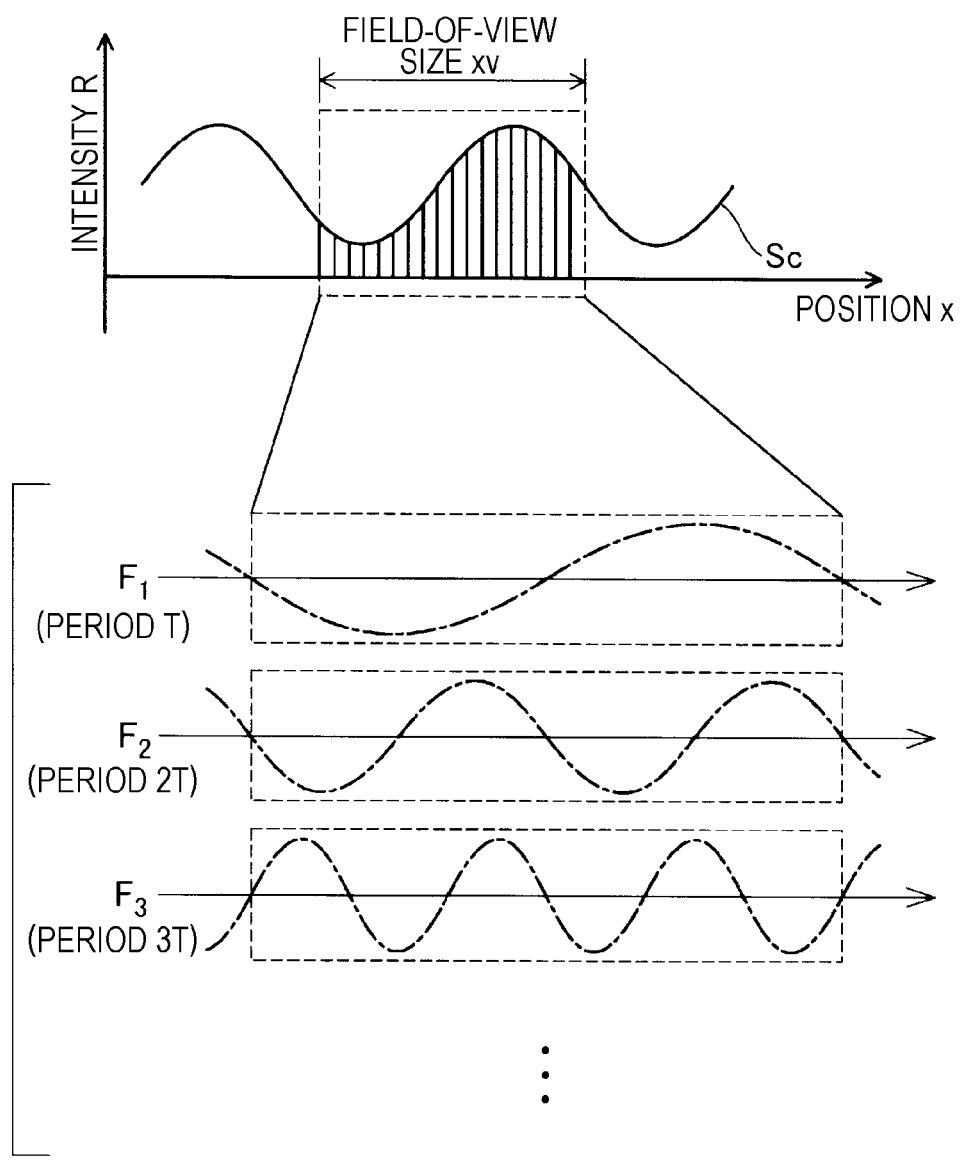
FIG. 6 is a graph for describing why a notch occurs in the frequency signal of the first comparative example.

FIG. 6 is a graph for describing reasons why the notch in the frequency signal FSa of the first comparative example occurs. In the upper side of FIG. 6, a graph representing an example of a light reception signal Sc output from the photosensor 47 in the optical scanning device of the first comparative example is illustrated. The horizontal axis of the graph represents a position x where the photosensor scans and the vertical axis represents intensity R of reflected light.

In the light reception signal Sc, as illustrated in the lower side of FIG. 6, frequency components $F_1, F_2, F_3, \ldots$ having a period T which is equivalent to the opening width xv of the photosensor or a period of an integer multiple of the period T are included. In the frequency components $F_1, F_2, F_3, \ldots$, the luminance obtained as a result of a spatial integration by the FFT is 0. This means that there is a possibility that the spatial frequency sensitivity (in the following, simply referred to as "sensitivity") to the frequency components $F_1, F_2, F_3, \ldots$ becomes 0 in the optical scanning device of the first comparative example. Existence of the specific frequency at which the sensitivity becomes 0 is considered to cause the occurrence of the notch in the frequency signal as illustrated in FIG. 5. Accordingly, it may be said that information is insufficient or missing in the frequency (or frequencies) at which the notch exists in the frequency signal.

Figure 7:
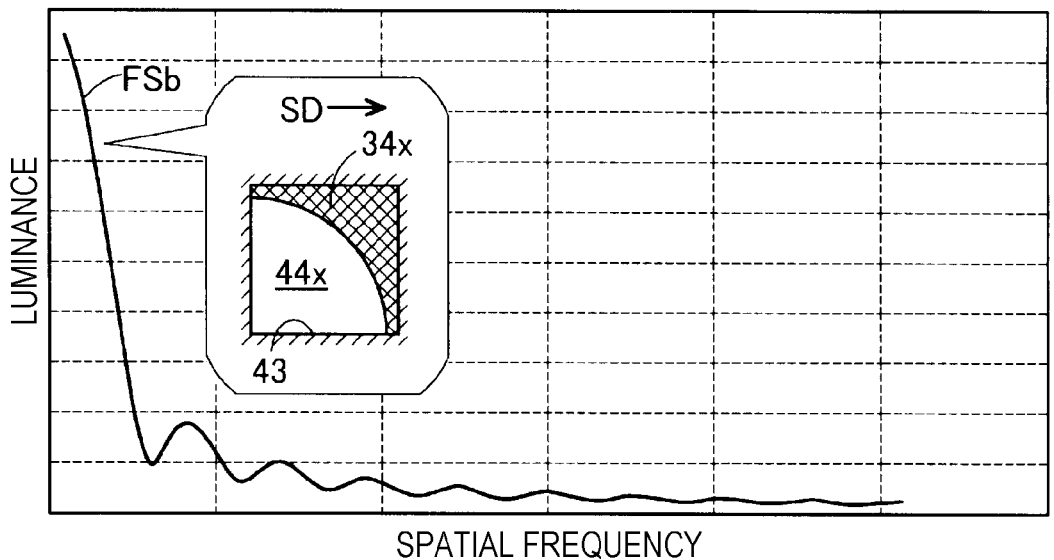
FIG. 7 is a graph illustrating an example of a frequency signal acquired in an optical scanning device of a second comparative example.

FIG. 7 is a graph illustrating a second comparative example of a frequency signal FSb acquired in an optical scanning device that has almost the same configuration as that of the optical scanning device 20 of the first embodiment except that a mask member 34x is attached to the opening portion 43 of the reflection unit 33 so as to form a mask opening 44x having a quadrant-shaped opening shape as illustrated in the balloon. The example of FIG. 7 is obtained when the same medium as that, which is used when the frequency signal FS described with reference to FIG. 4 is obtained, is used as a scanning target.

In the frequency signal FSb acquired in the optical scanning device of the second comparative example, although a decline of luminance to 0 is restrained, the luminance is changed upward and downward in a wave shape with respect to the spatial frequency. The result means that the mask member 34x is unable to sufficiently restrain the occurrence of the notch in a frequency signal obtained by changing only a width of a field of view of the photosensor in the orthogonal direction of the scanning direction SD. Even when the opening shape of the mask opening 44x is not a quadrant shape, but a circle shape, a result nearly similar to the case of the quadrant shape is obtained.

As illustrated in FIG. 4, occurrence of the notch described with reference to FIG. 5 to FIG. 7 is restrained in the frequency signal FS obtained in the optical scanning device 20 of the first embodiment. This is because, as will be described with reference to FIG. 8 and FIG. 9, the field of view of the photosensor 47 is specified by the mask opening 44 having the contour curve OC in the optical scanning device 20 of the first embodiment.

Figure 8:
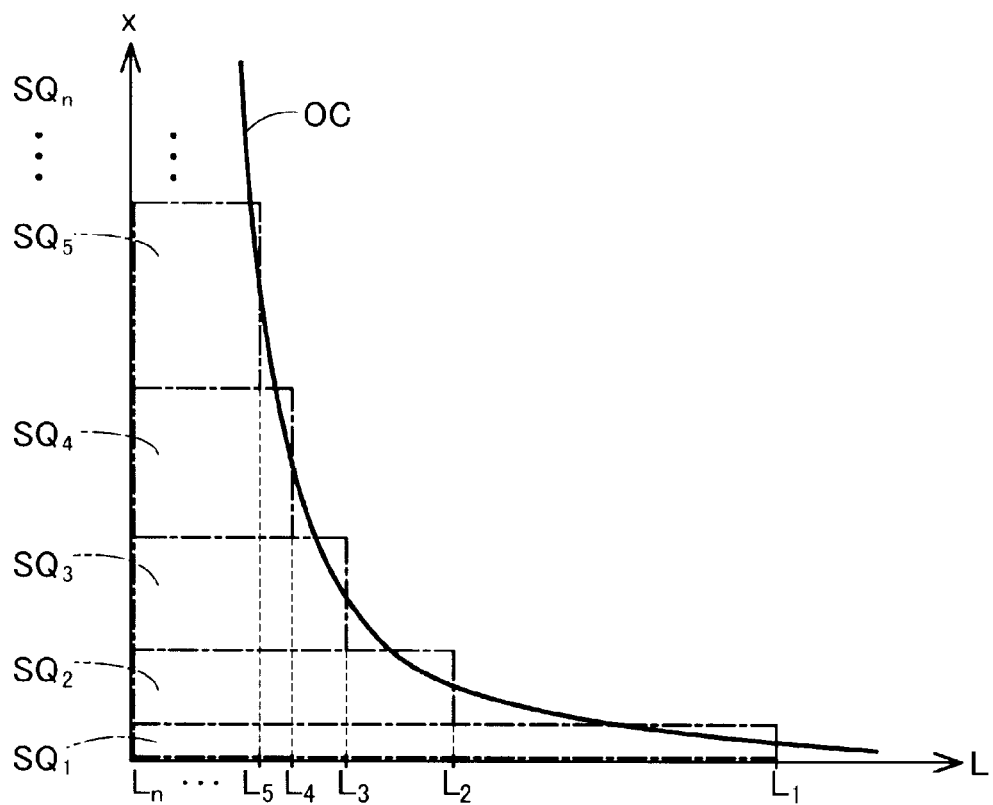
FIG. 8 is a graph for describing a contour curve in the mask opening.

FIG. 8 is a graph for describing the contour curve OC in the mask opening 44. The contour curve OC of the mask opening 44 is a curve which is set to allow the mask opening 44 to be divided into a plurality of minute regions $SQ_1$, $SQ_2$, ..., $SQ_n$ (n is a natural number of 2 or more). Each minute region has a substantially quadrilateral shape as will be described below. The minute regions $SQ_1$ to $SQ_n$ have areas which are equivalent to each other, respectively, and are continuously arranged adjacent to each other in a direction orthogonal to the scanning direction SD. Respective minute regions $SQ_1$ to $SQ_n$ extend from the contour curve OC to the first side portion 51 which corresponds to predetermined coordinate positions in the scanning direction SD. All of opening widths $L_1$ to $L_n$ which are widths of respective minute regions $SQ_1$ to $SQ_n$ in the scanning direction SD are different from one another.

The contour curve OC, which allows the mask opening 44 to be divided into the minute regions $SQ_1$ to $SQ_n$, is approximately represented by the following equation (1) when the coordinate in the scanning direction is set as L and the coordinate in the direction orthogonal to the scanning direction is set as x, $$L = A \cdot (B \cdot x)^\alpha + C \quad (1)$$

A, B: arbitrary positive number, C: arbitrary real number, α: arbitrary negative number.

Figure 9:
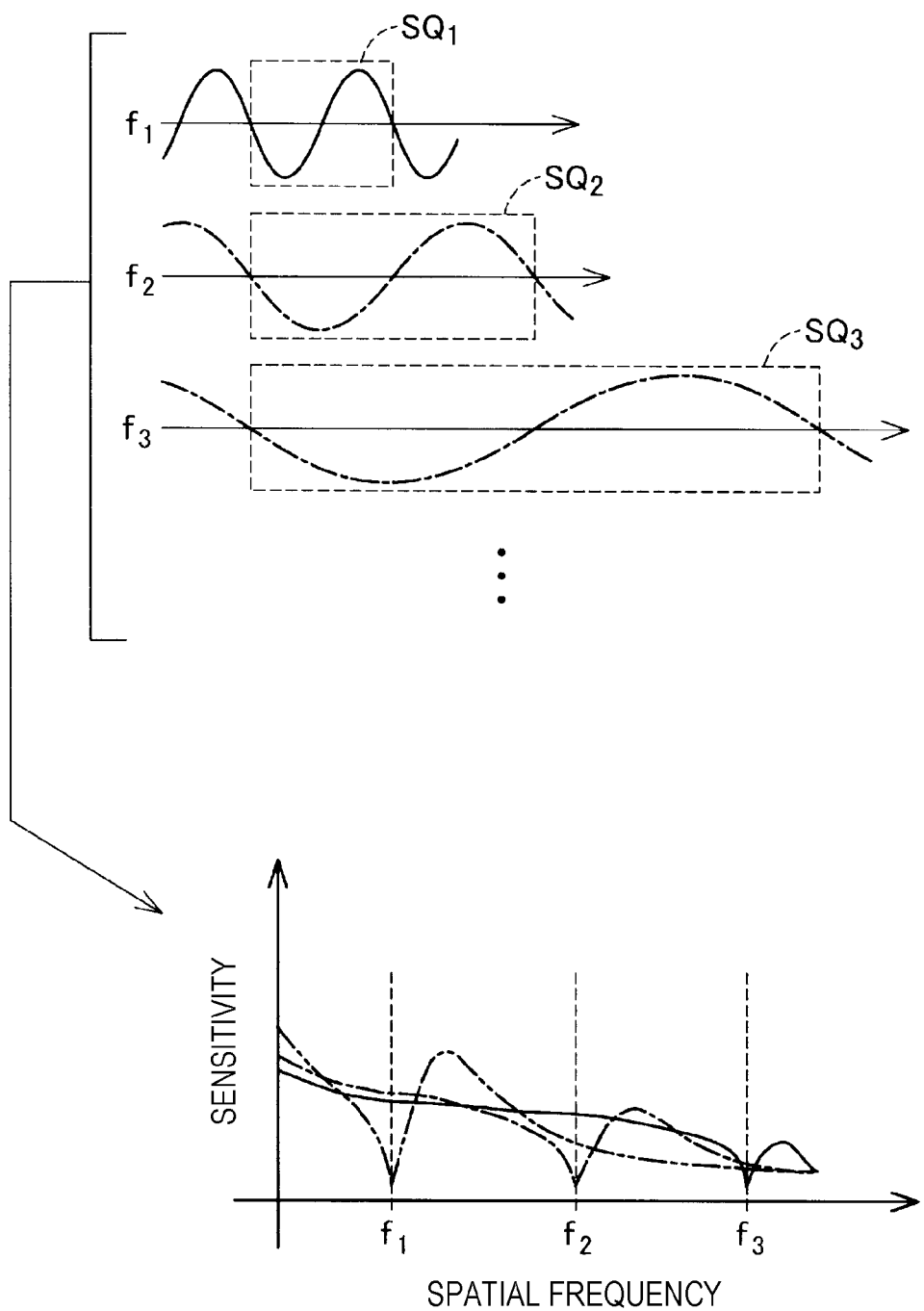
FIG. 9 is a graph for describing a principle that restrains occurrence of the notch in the frequency signal.

FIG. 9 is a graph for describing a principle that restrains the occurrence of the notch in the frequency signal FS when the mask opening 44 includes the contour curve OC described above. As described above, the opening region in the mask opening 44 is a region formed by integrating the minute regions $SQ_1$ to $SQ_n$ that are field of view regions having various opening widths $L_1$ to $L_n$, respectively. Areas of the opening of the minute regions $SQ_1$ to $SQ_n$ are equivalent to each other as described above and thus, amounts of light energy obtained by the photosensor 47 from respective minute regions $SQ_1$ to $SQ_n$ are constant. Accordingly, the frequency signal FS obtained from reflected light passing through the mask opening 44 corresponds to a frequency signal obtained by combining the frequency signals $FS_1$ to $FS_n$ obtained in respective minute regions $SQ_1$ to $SQ_n$.

Because all of the opening widths $L_1$ to $L_n$ of the minute regions $SQ_1$ to $SQ_n$ are different from one another, the frequencies at which the result of the spatial integration described with reference to FIG. 6 becomes 0 are different. That is, the frequencies at which sensitivity becomes 0 are different for each of the minute regions $SQ_1$ to $SQ_n$ (upper side of FIG. 9). That is, it means that the frequencies $f_1$, $f_2$, ..., $f_n$ at which the notch occurs in the minute regions $SQ_1$ to $SQ_n$ are different from one another. Accordingly, in the frequency signal FS which is a composite signal of the frequency signals $FS_1$ to $FS_n$, the notches occurring in the signals $FS_1$ to $FS_n$ are cancelled by corresponding frequency components in the other frequency signals (lower side of FIG. 9).

As such, in the optical scanning device 20 of the first embodiment, the mask opening 44 has the contour curve OC, which makes it possible to divide the opening region into the minute regions $SQ_1$ to $SQ_n$ having various opening widths $L_1$ to $L_n$. When a scanning target is scanned through the mask opening 44 in the scanning direction SD in which the minute regions $SQ_1$ to $SQ_n$ extend, frequency signal components obtained in the minute regions $SQ_1$ to $SQ_n$ cancel the notches occurring in the frequency signal components. Accordingly, the occurrence of the notch is restrained in the frequency signal FS which is output from the optical scanning device 20.

Here, a model in which it is assumed that the minute region $SQ_n$ is a region obtained by arranging n minute regions $SQ_1$, each of which having an opening width of 1/n, is considered. In the model, the equation (1) described above can be simply represented as the following equation (2). When the contour curve OC of the mask opening 44 is specified using the following equation (2), it is possible to more easily configure the mask opening 44 and increase specifying accuracy of the field of view region by the mask opening 44. Accordingly, it is possible to more reliably restrain the occurrence of the notch in the frequency signal FS.

$$L = (2 \cdot x)^{-1/2} \quad (2)$$

Figure 10:
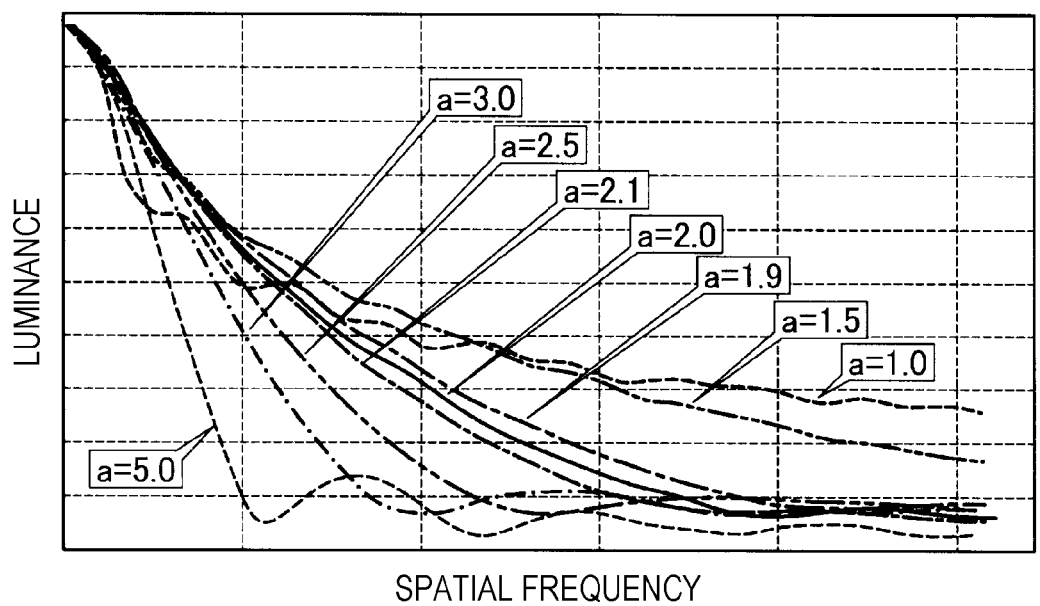
FIG. 10 is a graph illustrating an example of frequency signals when the contour curve is formed with various curves.

FIG. 10 is a graph illustrating an example of a frequency signal FS when the contour curves OC of the mask opening 44 are formed by various curves obtained by varying a value of the variable a of the following equation (3). The respective examples of FIG. 10 are obtained when the same medium as that, which is used when the frequency signal FS described with reference to FIG. 4 is obtained, is used as a scanning target.

$$L = (2 \cdot x)^{-1/a} \quad (3)$$

$$a = \{1.0, 1.5, 1.9, 2.0, 2.1, 2.5, 3.0, 5.0\}$$

In a case where the contour curve OC is configured by a curve of which the variable a is 5.0 in the equation (3) described above, the occurrence of the notch in which the luminance declines to 0 is restrained. The frequency signal which is made gentler compared with the comparative examples described with reference to FIG. 5 and FIG. 7 is obtained. In a case where the variable a is set as 3.0, a frequency signal which is gentler than the case where the variable a is 5.0 is obtained and in a case where the variable a is set as 2.5, a frequency signal which is gentler than the case where the variable a is 3.0 is obtained.

In a case where the variable a is set as 2.1 or 1.9, a frequency signal approximating a quadratic curve is obtained and further, in a case where the variable a is set as 2.0, a frequency signal approximating the quadratic curve is obtained. In a case where the variable a is set as 1.9, a frequency signal in which luminance is high in its entirety than the case where the variable a is set as 2.1 or 2.0 is obtained. In a case where the variable a is set as 1.5, the luminance in a frequency signal becomes higher than when the variable a is set as 1.9. In a case where the variable a is set as 1.0, the luminance in a frequency signal becomes higher than when the variable a is set as 1.5. However, blur occurs often in the luminance when the variable a is set as 1.0 compared to when the variable a is set as 1.5.

In order to increase the sensitivity while reducing the occurrence of a notch in the frequency signal, it is preferable that the variable a be a real number less than 5.0. The variable a may be less than or equal to 3.0 and the variable a may be less than or equal to 2.5. It is preferable that the variable a be less than or equal to 2.1 than the variable a be greater than or equal to 2.1. In a case where it is intended to further enhance sensitivity, it is preferable that the variable a be less than or equal to 2.0 or less than or equal to 1.9. It is preferable that the variable a be less than or equal to 1.5. The variable a may be less than or equal to 1.0. It is preferable that the variable a be selected in a range that is less than 5.0 or less than 3.0 or less than 2.1 or less than 2.0 or less than 1.9 or less than 1.5 or less than 1.0 in the context of increasing sensitivity.

On the other hand, in a case where it is intended to obtain a frequency signal with less blur while securing or ensuring sensitivity, it is preferable that the variable a be greater than or equal to 1.0 and it is more preferable that the variable a be greater than or equal to 1.5. It is preferable that the variable a may be greater than or equal to 1.9 and it is more preferable that the variable a be 2.0 or greater. Thus, the sensitivity and amount of blur can be balanced by selecting an appropriate variable a.

In order to obtain a frequency signal FS approximating the quadratic curve and having less blur, the variable a may be greater than or equal to 1.0 and less than or equal to 3.0. It is preferable that the variable a be greater than or equal to 1.5 and less than or equal to 2.5. Furthermore, it is preferable that the variable a be greater than or equal to 1.9 and less than or equal to 2.1. It is preferable that the variable a be 2.0.

As described above, according to the optical scanning device 20 of the first embodiment, it is possible to obtain the frequency signal FS (FIG. 4) in which the occurrence of a notch (or notches) is restrained. Because the occurrence of the notch is restrained in the frequency signal FS, a decrease in the sensitivity in specific frequency components is also restrained. Accordingly, according to the optical scanning device 20 of the first embodiment, it is possible to more accurately ascertain the features based on an appearance configuration appearing on a surface of the printing paper PP, material of the printing paper PP, an internal structure, or the like in a state where missing or insufficiency of information is reduced. The information contained in the frequency signal FS is insufficient when a notch is present or when the a luminance value is zero or when the luminance changes upwardly and downwardly in a wave shape. Embodiments of the invention ensure that the frequency signal FS contains sufficient information.

According to the optical scanning device 20 of the first embodiment, the frequency signal FS is obtained as a signal which renders a curve graph in which the luminance is gradually decreased as the spatial frequency is increased. The frequency signal FS obtained in this manner is a simple signal and it is easier to interpret the frequency signal or make corrections. It is also possible to reduce an amount of data associated with the signal. Especially, when the signal is a signal rendering a curve graph approximating the quadratic curve, the curve graph is easily converted into a flat graph Cs as illustrated in FIG. 4 by the correction performed using the quadratic function. In the printing apparatus 10 of the first embodiment, as will be described below, a transport amount of the printing paper PP used for the transport control in the transport device 12 is acquired using the frequency signal FS acquired by the optical scanning device 20. In some embodiments, the frequency signal FS can be used to determine, by way of example and not limitation, various aspects or parameters of the transport including the amount that the printing paper PP is transported.

Figure 11:
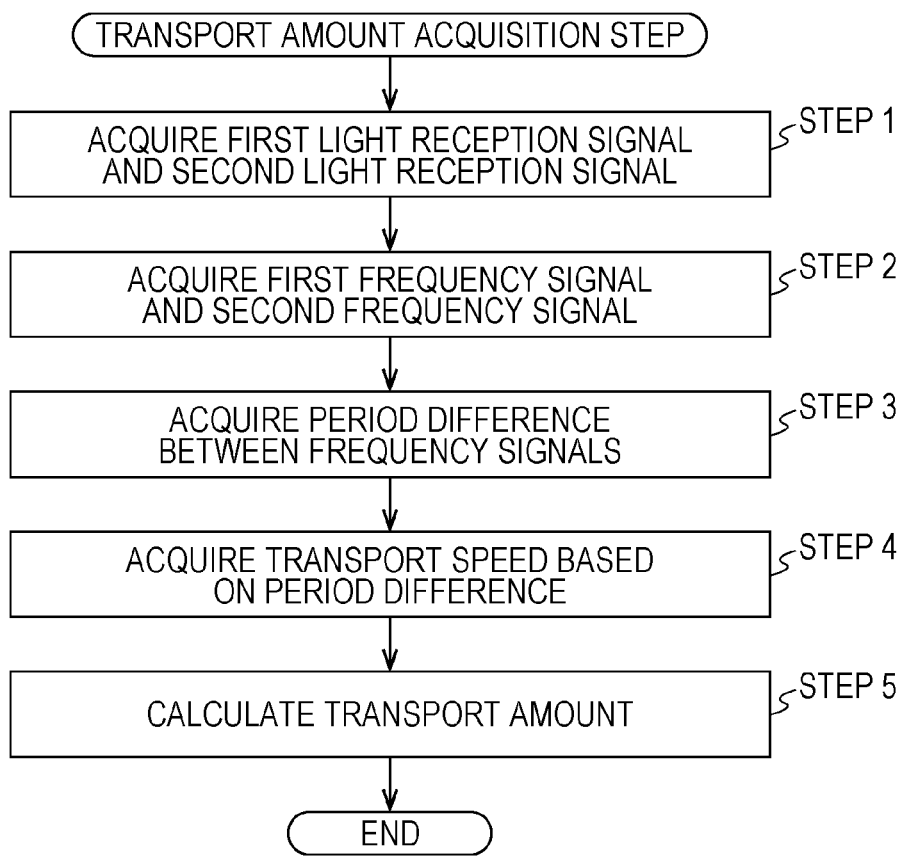
FIG. 11 is a flowchart illustrating a flow of a transport amount acquisition step of a printing paper in the printing apparatus.

FIG. 11 is a flowchart illustrating a flow of a transport amount acquisition step of the printing paper PP in the printing apparatus 10. FIG. 11 illustrates a method for determining a transport amount. The transport amount acquisition method or steps thereof is executed in association with a printing paper PP transport step in print processing of the printing apparatus 10. Respective steps to be described in the following are repeated at the sampling period described above.

In Step 1, the first light reception signal Sd1 and the second light reception signal Sd2 are acquired in the optical scanning device 20. Specifically, the photosensor 47 of the first detection unit 21 receives reflected light such that the first light reception signal Sd1 is generated and output to the signal generation unit 25. Similarly, the photosensor 47 of the second detection unit 22 receives reflected light such that the second light reception signal Sd2 is generated and output to the signal generation unit 25.

In Step 2, the first frequency signal FS1 and the second frequency signal FS2 are generated and output to the control unit 11 by performing an FFT on each of the first light reception signal Sd1 and the second light reception signal Sd2 by the signal generation unit 25. The control unit 11 may correct the two acquired frequency signals FS1 and FS2 and store the frequency signals FS1 and FS2 in a storage device.

In the first embodiment, as described above, the frequency signal FS is acquired as a signal rendering a curve that approximates a quadratic curve and thus, the control unit 11 easily converts the frequency signal FS into a signal CS. In the signal CS, a width of change in the luminance with respect to the spatial frequency is small by the correction performed using a quadratic function (FIG. 4), which may be predetermined. Both pieces of correction data obtained by correcting the first frequency signal FS1 and the second frequency signal FS2 are, as described above, stored as a first signal group SG1 and a second signal group SG2 in the control unit 11, respectively, in a state where time-series order of acquisition of the signals is maintained.

In Step 3, the control unit 11 interprets a pattern of a temporal change regarding each of the first signal group SG1 and the second signal group SG2. Specifically, the control unit 11 acquires a specific signal value for each of the signal groups SG1 and SG2 or a period at which a pattern of change of the specific signal value repeatedly appears. A period difference ΔT representing a shift of a period between the first signal group SG1 and the second signal group SG2 is calculated.

In Step 4, the control unit 11 derives a transport amount of the printing paper PP based on the period difference ΔT. Specifically, the control unit 11 calculates a transport speed PV of the printing paper PP using the period difference calculated in Step 3 and a separation distance DD (FIG. 1) between the first detection point DPa and the second detection point DPb (equation (4) described below).

$$PV=DD/\Delta T \quad (4)$$

In Step 5, the control unit 11 integrates the transport speed PV to thereby calculate the transport amount of the printing paper PP and outputs the transport amount to the transport control unit 18. As described above, the transport control unit 18 controls a rotation driving of the motor of the winding unit 16 based on the transport amount to transport the printing paper PP. Thus, it is possible to increase position accuracy of the printing paper PP with respect to where ink dots are recorded and it is possible to thereby and enhance the image quality of the printing image.

As described above, according to the optical scanning device 20 of the first embodiment, it is possible to acquire the frequency signal FS in which the occurrence of a notch (or other loss of information) is restrained. According to the transport device 12 of the first embodiment, it is possible to easily and accurately acquire the transport amount of the printing paper PP based on the frequency signal FS and increase the transport accuracy of the printing paper PP. According to the printing apparatus 10 of the first embodiment, the transport accuracy of the printing paper PP is increased to thereby make it possible to enhance the image quality of the printing image. In addition, the optical scanning device 20, the transport device 12, and the printing apparatus 10 of the first embodiment are able to exhibit various working effects described in the embodiment.

Second Embodiment

Figure 12:
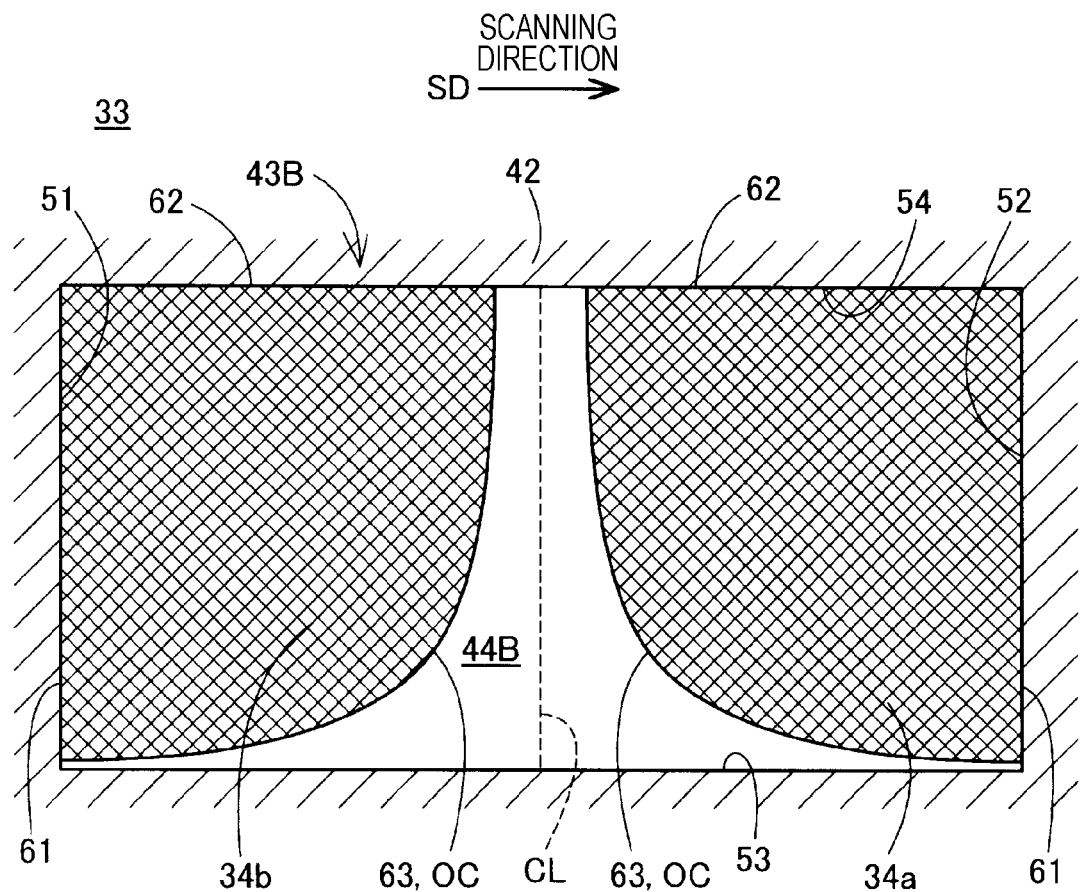
FIG. 12 is a schematic diagram illustrating a mask opening in a second embodiment.

FIG. 12 is a schematic diagram illustrating a mask opening 44B provided in an optical scanning device of a second embodiment of the invention. The optical scanning device of the second embodiment has almost the same configuration as the optical scanning device 20 of the first embodiment except that an opening shape of the mask opening 44B is different from that of the first embodiment, and is able to be incorporated into a printing apparatus or a transport device having a configuration similar to that of the printing apparatus 10 or the transport device 12 described in the first embodiment.

In the optical scanning device of the second embodiment, the opening portion 43B provided in the reflection unit 33 is almost the same as the opening portion 43 of the first embodiment except that a width in the scanning direction SD is twice the width of the opening portion 43. The opening portion 43B has four side portions 51 to 54 which are similar to those of the opening portion 43 of the first embodiment. A first mask member 34a and a second mask member 34b are disposed in the opening portion 43B. The first mask member 34a and the second mask member 34b could be an integrated mask.

The first mask member 34a has a configuration similar to the mask member 34 of the first embodiment and has a first end portion 61, a second end portion 62, and a third end portion 63. The second mask member 34b has a mirror-symmetrical shape. That is, the second mask member 34b has the same shape as that obtained by turning the first mask member 34a upside down. The second mask member 34b has three end portions 61 to 63 which respectively correspond to the end portions 61 to 63 of the first mask member 34a. The second mask member 34b may be identical to the first mask member 34a, but is oriented or placed in the opening 43B differently The first mask member 34a and the second mask member 34b are arranged in the scanning direction SD in such a way that the third end portions 63, which configure the contour curve OC, of the first mask member 34a and the second mask member 34b face each other. The first mask member 34a is disposed in such a way that the first end portion 61 of the first mask member 34a is disposed in close contact with the second side portion 52 of the opening portion 43B. The second mask member 34b is disposed in such a way that the first end portion 61 of the second mask member 34b is disposed in close contact with the first side portion 51 of the opening portion 43B. Thus, the mask opening 44B having an opening shape which is symmetrical in the scanning direction is formed in the opening portion 43B. The mask opening 44B has two contour curves OC which are in mirror symmetry so as to sandwich the center line CL of opening portion 43B in the scanning direction SD. The two contour curves correspond to subordinate concepts of the first contour curve and the second contour curve in embodiments of the invention, respectively. In the second embodiment, two regions between each contour curve OC and the center line CL can be divided into the minute regions $SQ_1$, $SQ_2$, . . . , $SQ_n$ described in the first embodiment in the opening region within the mask opening 44B, respectively.

Figure 13:
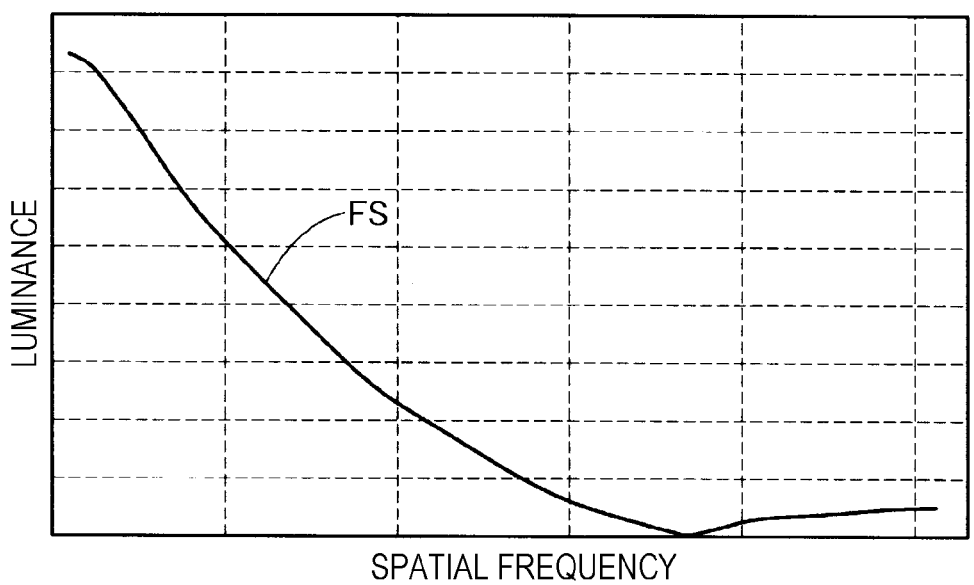
FIG. 13 is a graph illustrating an example of a frequency signal in the second embodiment.

FIG. 13 is a graph illustrating an example of the frequency signal FS obtained by the optical scanning device of the second embodiment. Also, in the optical scanning device of the second embodiment, the occurrence of a notch where sensitivity at a specific frequency sharply declines to 0 in the frequency signal FS is restrained. For that reason, similar to the optical scanning device 20 of the first embodiment, a detection accuracy of the features appearing on appearance or the like in the scanning target is increased. In addition, according to the optical scanning device of the second embodiment, in the transport device and the printing apparatus that include the optical scanning device, it is possible to exhibit various working effects similar to those described in the first embodiment.

Third Embodiment

Figure 14:
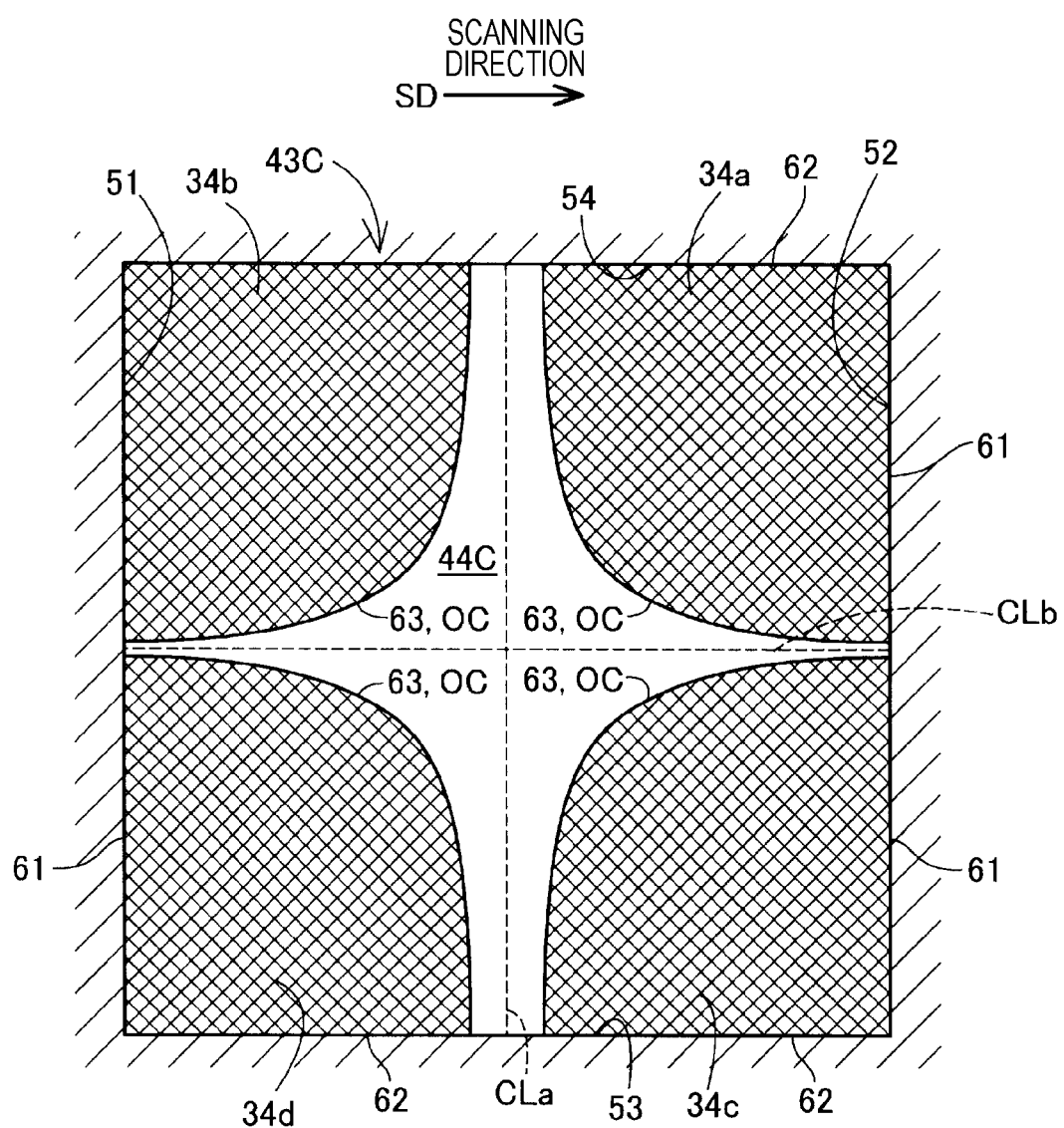
FIG. 14 is a schematic diagram illustrating a mask opening in a third embodiment.

FIG. 14 is a schematic diagram illustrating a mask opening 44C provided in an optical scanning device in a third embodiment of the invention. In FIG. 14, a center line CLa of the opening portion 43B in the scanning direction SD and a center line CLb of the opening portion 43B in a direction orthogonal to the scanning direction SD are illustrated. The optical scanning device of the third embodiment has almost the same configuration as the optical scanning device of the second embodiment except that an opening shape of the mask opening 44C is different, and is able to be incorporated into a printing apparatus or a transport device having a configuration similar to that of the printing apparatus 10 or the transport device 12 described in the first embodiment.

In the optical scanning device of the third embodiment, the opening portion 43C of the reflection unit 33 has almost the same configuration as the opening portion 43B of the second embodiment except that the opening width is twice that of the opening portion 43B in a direction orthogonal to the scanning direction SD, and has four side portions 51 to 54 which are similar to those of the opening portion 43B. In the opening portion 43C, a third mask member 34c and a fourth mask member 34d are disposed in addition to the first mask member 34a and the second mask member 34b. The third mask member 34c is mirror symmetric to the first mask member 34a in a direction orthogonal to the scanning direction SD. The fourth mask member 34d is mirror symmetric to the second mask member 34b in a direction orthogonal to the scanning direction SD.

The mask opening 44C of the third embodiment has two contour curves OC which are provided in the third mask member 34c and the fourth mask member 34d, respectively, in addition to two contour curves OC which are provided in the first mask member 34a and the second mask member 34b, respectively. The two contour curves OC correspond to subordinate concepts of the third contour curve and the fourth contour curve in the invention, respectively. The mask opening 44C of the third embodiment has a substantially cross-shaped opening shape which is symmetrical in each of the scanning direction SD and the orthogonal direction orthogonal to the scanning direction SD. In the third embodiment, four regions surrounded by respective contour curves OC, the center line CLa, and the center line CLb can be divided into the minute regions $SQ_1$, $SQ_2$, ..., $SQ_n$ described in the first embodiment in the opening region within the mask opening 44C, respectively.

Figure 15:
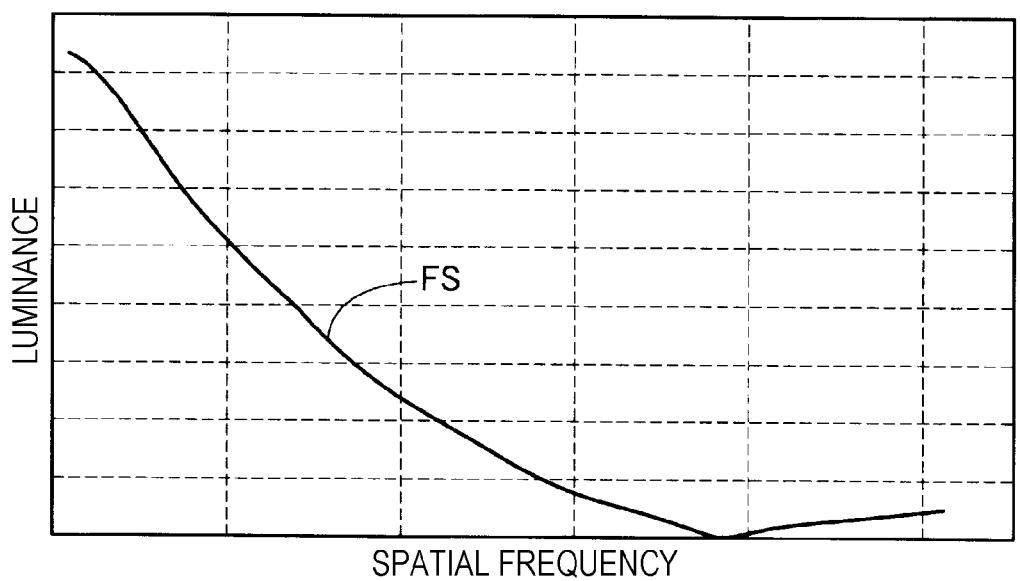
FIG. 15 is a graph illustrating an example of a frequency signal in the third embodiment.

FIG. 15 is a graph illustrating an example of the frequency signal FS obtained by the optical scanning device of the third embodiment. According to the optical scanning device of the third embodiment, the occurrence of the notch where sensitivity at a specific frequency sharply declines to 0 in the frequency signal FS is restrained, similar to the optical scanning device of the second embodiment. In addition, according to the optical scanning device of the second embodiment, the transport device, and the printing apparatus that includes the optical scanning device, it is possible to exhibit various working effects similar to those described in the first embodiment or the second embodiment.

Fourth Embodiment

Figure 16:
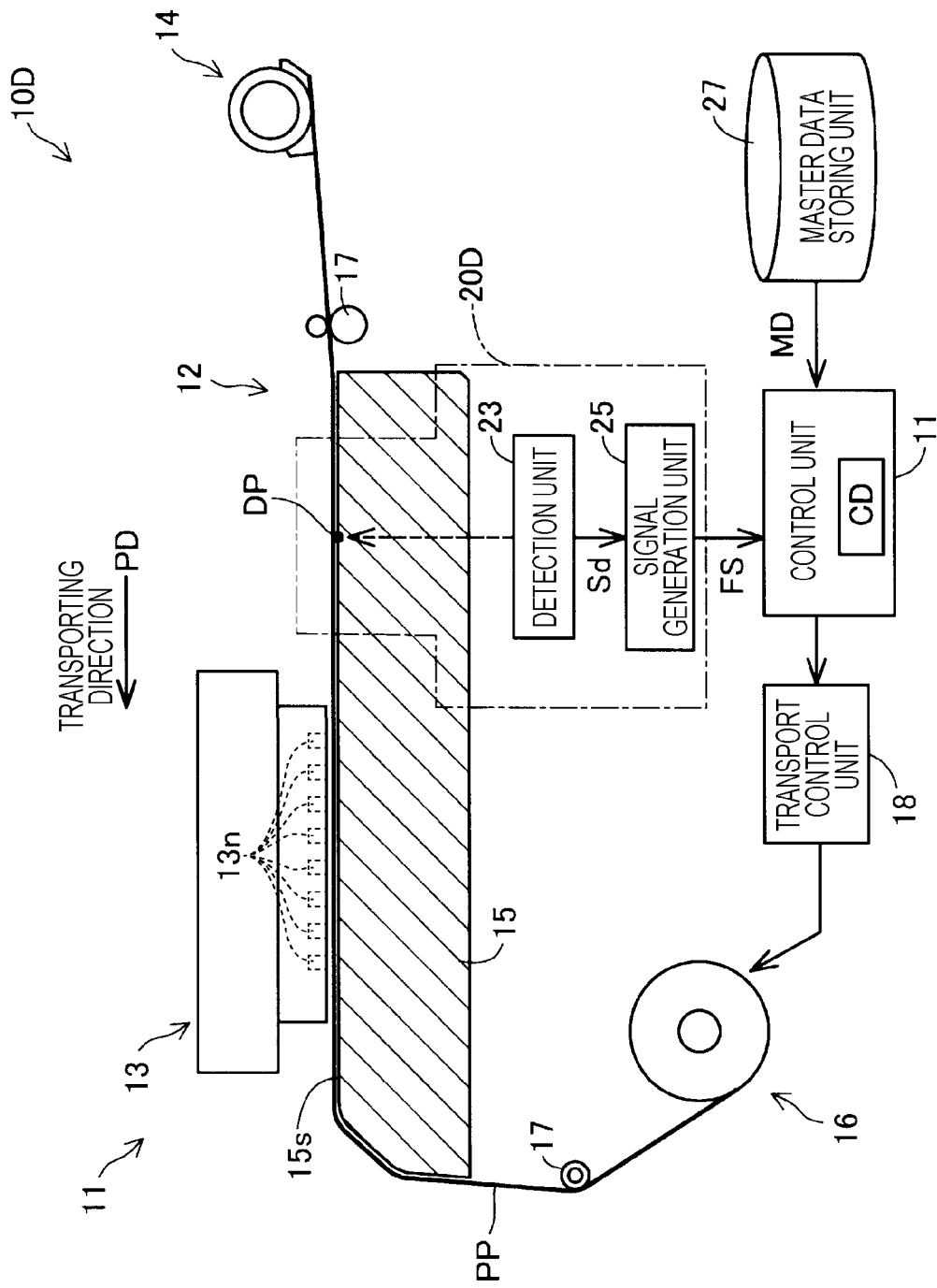
FIG. 16 is a schematic diagram illustrating a configuration of a printing apparatus in a fourth embodiment.

FIG. 16 is a schematic diagram illustrating a configuration of a printing apparatus 10D including an optical scanning device as a fourth embodiment of the invention. The configuration of the printing apparatus 10D of the fourth embodiment is almost the same as that of the printing apparatus 10 of the first embodiment except that the transport device 12 includes an optical scanning device 20D of the fourth embodiment and a master data storing unit 27. The printing apparatus 10D of the fourth embodiment has a function as a feature detection device that detects a feature representing the feature of the printing paper PP, and executes a paper-type determination processing for determining a type of the printing paper PP being transported based on the feature detected from a surface side of the detected printing paper PP. In one example, the printing apparatus 10D includes a function of determining a type of the printing paper PP based on the frequency signal.

The optical scanning device 20D of the fourth embodiment irradiates scanning light toward the rear surface of the printing paper PP in or at a detection point DPa of the base surface 15s which configures the transport path of the printing paper PP, generates a frequency signal FS representing the feature detected from the rear surface side of the printing paper PP, and outputs the frequency signal FS to the control unit 11. The optical scanning device 20D includes a single detection unit 23 having the same configuration as that of the first detection unit 21 or the second detection unit 22 described in the first embodiment.

The detection unit 23 includes the mask opening 44 through which reflected light passes as described in the first embodiment (FIG. 3). The detection unit 23 scans the printing paper PP at a predetermined sampling period and outputs the light reception signal Sd. The signal generation unit 25 of the optical scanning device 20D performs an FFT on the light reception signal Sd output from the detection unit 23 and outputs the frequency signal FS (FIG. 4) similar to that described in the first embodiment to the control unit 11.

The control unit 11 stores the frequency signal FS, which is output from the optical scanning device 20D at the predetermined sampling period, as feature data CD detected from the printing paper PP in a storage device (not illustrated) in time-series order. Feature data CD which is a data group of the frequency signal FS stored in time-series order corresponds to a subordinate concept of feature data in the invention. The control unit 11 in the fourth embodiment corresponds to a subordinate concept of a feature data acquisition unit in the invention.

In the master data storing unit 27, a database of master data obtained by collecting the feature data of each type of the printing paper PP is constructed. The master data may include data feature data for a plurality of paper types. In the type-of-printing paper determination processing, the control unit 11 reads the master data from the master data storing unit 27, collates the master data with the feature data CD, and specifies a type of the printing paper PP. In effect, the feature data derived from the frequency signal is compared with the master data. The type of paper is determined based on which master data matches or substantially matches the collected feature data.

In the frequency signal FS obtained by the optical scanning device 20D of the fourth embodiment, the occurrence of the notch is restrained and missing or insufficiency of information is restrained, as described in the first embodiment. Accordingly, the frequency signal FS is used such that determination accuracy is increased in the type-of-printing paper determination processing. In addition, according to the optical scanning device 20D of the fourth embodiment, the transport device 12, and the printing apparatus 10D that include the optical scanning device 20D, it is possible to exhibit various working effects similar to those described in the respective embodiments described above.

Fifth Embodiment

Figure 17:
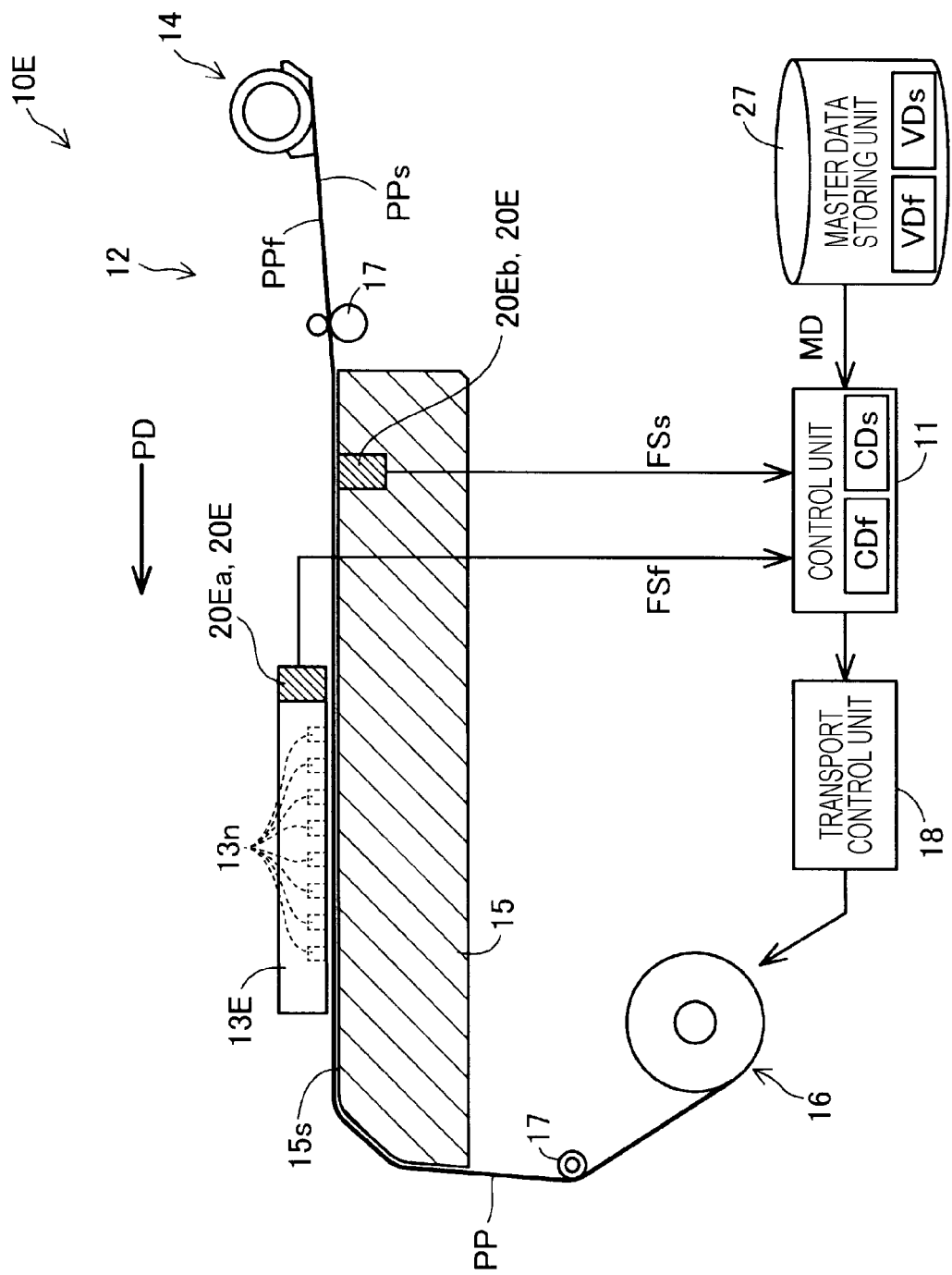
FIG. 17 is a schematic diagram illustrating a configuration of a printing apparatus in a fifth embodiment.

FIG. 17 is a schematic diagram illustrating a configuration of a printing apparatus 10E including a feature detection device as a fifth embodiment of the invention. A configuration of the printing apparatus 10E of the fifth embodiment is almost the same as that of the printing apparatus 10D (FIG. 16) of the fourth embodiment except for matters which will be described in the following. The printing apparatus 10E includes a scanning unit 20E that scans the printing paper PP on the transport path of the printing paper PP. In the printing apparatus 10E, the scanning unit 20E, the control unit 11, and the master data storing unit 27 are associated with each other and function as a medium determination device configured to determine the type of the printing paper PP which is a medium.

The scanning unit 20E includes a first surface scanning unit 20Ea and a second surface scanning unit 20Eb. Each of the first surface scanning unit 20Ea and the second surface scanning unit 20Eb has a configuration similar to that of the optical scanning device 20D (FIG. 16) of the fourth embodiment and includes the detection unit 23 and the signal generation unit 25. The first and second scanning units may use their own or the same detection unit and signal generation unit. In FIG. 17, illustration of the detection unit 23 and the signal generation unit 25 is omitted for convenience. The first surface scanning unit 20Ea and the second surface scanning unit 20Eb may also be configured as, for example, a multi-microsensor and may be capable of sensing or determining multiple parameters.

The first surface scanning unit 20Ea scans a first surface PPf of the printing paper PP by incoherent scanning light. The second surface scanning unit 20Eb scans a second surface PPs of the printing paper PP using incoherent scanning light. In the fifth embodiment, the first surface PPf of the printing paper PP is a printing surface opposing a printing head unit 13E and the second surface PPs is the rear surface located at a side opposite to the printing surface. In the fifth embodiment, the first surface scanning unit 20Ea is attached to the printing head unit 13E and the second surface scanning unit 20Eb is embedded in the support base 15 functioning as a platen.

Figure 18B:
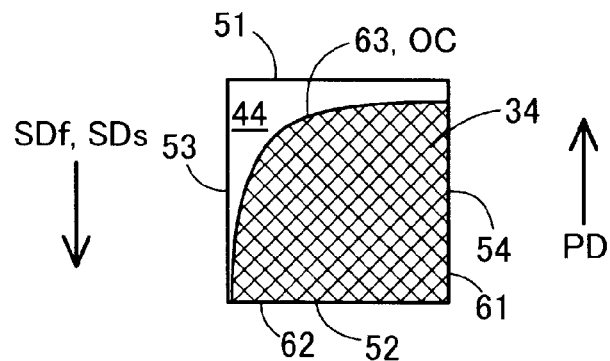
FIG. 18B is a schematic diagram illustrating a direction of a mask opening of the fifth embodiment.

The configurations of the first surface scanning unit 20Ea and the second surface scanning unit 20Eb will be described with reference to FIG. 18A and FIG. 18B. FIG. 18A is a diagram illustrating more specific arrangement configurations of the first surface scanning unit 20Ea and the second surface scanning unit 20Eb. In FIG. 18A, a region in the vicinity of the printing head unit 13E in the printing apparatus 10E is extracted and illustrated. In FIG. 18B, the mask opening 44 of each of the first surface scanning unit 20Ea and the second surface scanning unit 20Eb is illustrated.

The printing apparatus 10E is a line printer and the printing head unit 13E is installed in a direction intersecting with the transporting direction PD of the printing paper PP above the transport path of the printing paper PP (FIG. 18A). More specifically, the printing head unit 13E is disposed along a direction orthogonal to the transporting direction PD.

As described above, in the fifth embodiment, the first surface scanning unit 20Ea is attached to the printing head unit 13E. The first surface scanning unit 20Ea emits scanning light toward the first surface PPf of the printing paper PP from above the printing paper PP which is transported. The scanning direction SDf of the first surface scanning unit 20Ea is a direction opposite to the transporting direction PD.

The first surface scanning unit 20Ea includes the mask opening 44 for taking or receiving reflected light (e.g., scanning light reflected on or from the first surface PPf of the printing paper PP) (FIG. 18A and FIG. 18B). The mask opening 44 is provided on a surface opposing the printing paper PP of the first surface scanning unit 20Ea. An opening direction of the mask opening 44 is vertical to the first surface PPf of the printing paper PP which is a scanning target. The mask opening 44 is provided in such a way that the direction of the contour curve OC with respect to the scanning direction SDf becomes the same direction as that described in the first embodiment.

As described above, the second surface scanning unit 20Eb is embedded in the support base 15 (FIG. 18A). The second surface scanning unit 20Eb is provided at the upstream side of the printing head unit 13E in the transporting direction PD. The second surface scanning unit 20Eb emits scanning light toward the second surface PPs from below the printing paper PP which is being transported. The scanning direction SDs of the second surface scanning unit 20Eb is a direction opposite to the transporting direction PD, similar to the first surface scanning unit 20Ea.

The second surface scanning unit 20Eb includes the mask opening 44 for taking or receiving reflected light (e.g., scanning light reflected on or from the second surface PPs of the printing paper PP) (FIG. 18A and FIG. 18B). An opening direction of the mask opening 44 of the second surface scanning unit 20Eb is vertical to the second surface PPs of the printing paper PP which is a scanning target. The mask opening 44 of the second surface scanning unit 20Eb is provided in such a way that the direction of the contour curve OC with respect to the scanning direction SDs becomes the same direction as that described in the first embodiment. That is, in the fifth embodiment, the mask openings 44 of the first surface scanning unit 20Ea and the second surface scanning unit 20Eb are disposed in the same direction with respect to the transporting direction PD.

The scanning units 20Ea and 20Eb are preferably provided at the upstream side in the transporting direction PD with respect to the printing head unit 13E. Thus, a region to which ink will be adhered can be scanned and thus, it is possible to restrain the scanning results of the scanning units 20Ea and 20Eb from being influenced by bending, pollution or the like of the printing paper PP due to adhesion of inks. The first surface scanning unit 20Ea and the second surface scanning unit 20Eb are preferably provided at positions that are separated from each other. In one example, the scanning units 20Ea and 20Eb are separated with respect to at least the transport direction. Thus, it is possible to restrain scanning light or reflected light of the first surface scanning unit 20Ea and the second surface scanning unit 20Eb from interfering with each other.

The first surface scanning unit 20Ea outputs the frequency signal FSf generated as the result of the scanning to the control unit 11 at a predetermined period (FIG. 17). The second surface scanning unit 20Eb also outputs the frequency signal FSs generated as the result of the scanning to the control unit 11 at a predetermined period. The control unit 11 stores the frequency signals FSf and FSs in a storing unit (not illustrated) of or associated with the control unit 11 in time series, respectively, as a batch of groups.

The group of the frequency signals FSf acquired by the control unit 11 from the first surface scanning unit 20Ea represents the feature detected from the first surface PPf side of the printing paper PP. In the following, the group of the frequency signals FSf is also referred to as "first surface feature data CDf". The group of the frequency signals FSs acquired by the control unit 11 from the second surface scanning unit 20Eb represents the feature detected from the second surface PPs side of the printing paper PP. In the following, the group of the frequency signals FSs is also referred to as "second surface feature data CDs". As such, the control unit 11 has a function as the feature data acquisition unit in that the control unit 11 acquires the feature data CDs.

Pieces of master data prepared for each type of the printing paper PP in advance are stored in the database of the master data storing unit 27. The pieces of master data includes first surface collation data VDf which is a piece of master data corresponding to the first surface feature data CDf and second surface collation data VDs which is a piece of master data corresponding to the second surface feature data CDs. The first surface collation data VDf and the second surface collation data VDs are stored in sets in association with the type of the printing paper PP.

The control unit 11 functions as a determination processing unit and is configured to determine a type of a medium or a type of the paper PP. The control unit 11 executes first surface collation processing for collating the first surface feature data CDf with the first surface collation data VDf. The control unit 11 also executes second surface collation processing for collating the second surface feature data CDs with the second surface collation data VDs. The control unit 11 specifies the type of the printing paper PP based on a result of collations of both the first surface collation processing and the second surface collation processing.

Figure 19:
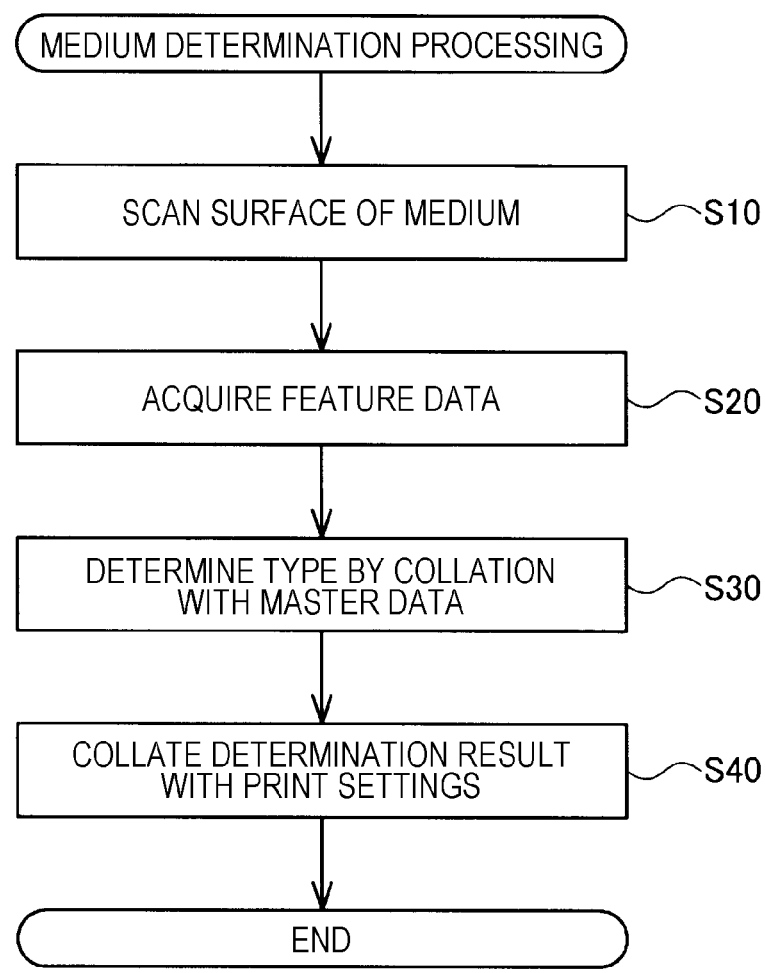
FIG. 19 is a flowchart illustrating a flow of medium determination processing.

FIG. 19 is a flowchart illustrating a flow of medium determination processing executed by the control unit 11 in the printing apparatus 10E. The medium determination processing is processing for determining the type of the printing paper PP based on the feature detected from the surface side of the printing paper PP detected by the scanning unit 20E. The control unit 11 may allow the medium determination processing to be automatically executed prior to the execution of print processing. Otherwise, the control unit 11 may also allow the execution of the medium determination processing to be started according to an instruction from a user.

In Step S10, the control unit 11 scans the first surface PPf and the second surface PPs of the printing paper PP with the first surface scanning unit 20Ea and the second surface scanning unit 20Eb, respectively. First, the control unit 11 causes the transport device 12 to transport the printing paper PP in the transporting direction PD by a predetermined distance. The control unit 11 may move the printing paper PP, for example, from several mm to several tens of mm. In the transport step, the printing paper PP is preferably transported in such a way that a time period, during which the printing paper PP is moved at almost constant speed, is caused.

The control unit 11 causes the first surface scanning unit 20Ea and the second surface scanning unit 20Eb to scan the first surface PPf and the second surface PPs of the printing paper PP, respectively, while the printing paper PP is transported. Scanning by the first surface scanning unit 20Ea and the second surface scanning unit 20Eb is preferably executed while the printing paper PP is moved at almost constant speed. This type of scanning may be performed in multiple embodiments. Further, the type of paper may be determined when using only one scanning unit in one embodiment.

In Step S20, the control unit 11 acquires the group of the frequency signals FSf, which are output by the first surface scanning unit 20Ea, as the first surface feature data CDf. The control unit 11 acquires the group of the frequency signals FSs, which are output by the second surface scanning unit 20Eb, as the second surface feature data CDs.

In Step S30, the control unit 11 references the database of the master data storing unit 27 and determines the type of the printing paper PP. The control unit 11 executes first surface collation processing for collating the first surface feature data CDf with the first surface collation data VDf of each type of the printing paper PP. The control unit 11 executes second surface collation processing for collating the second surface feature data CDs with the second surface collation data VDs of each type of the printing paper PP. The control unit 11 specifies a type, to which a set of pieces of collation data VDf and VDs belong, for which a collation ratio greater than or equal to a predetermined threshold value is obtained as a type of the printing paper PP being transported in both the first surface collation processing and the second surface collation processing.

In Step S40, the control unit 11 collates the determination result in Step S30 with the type of the printing paper PP included in a printing condition which is stored in the storing unit of the control unit 11 in advance. The printing condition is data in which various conditions to be applied to print processing of the printing apparatus 10E are set, and may be set by a user in advance. In a case where both the determination result and the type of the printing paper PP are not coincident with each other, the control unit 11 informs the user that the determination result is not coincident with the type of the printing paper PP. The control unit 11 may allow a message to be displayed on a display unit (not illustrated) of the printing apparatus 10E or an alarm by a voice to be issued. The control unit 11 may also allow the printing condition to be changed automatically according to the determination result of Step S40. In a case where a set of pieces of collation data VDf and VDs, for which it can be determined to be coincident with a set of pieces of feature data CDf and CDs, is not found among the sets of pieces of collation data VDf and VDs of the master data storing unit 27 in Step S30, the control unit 11 may also urge the user to register a new type of the printing paper PP.

In each of the frequency signals FSf and FSs output by the scanning unit 20E of the fifth embodiment, the occurrence of the notch is restrained due to the opening shape of the mask opening 44, similar to that described in the first embodiment. Accordingly, missing or insufficiency of information due to the occurrence of or associated with the notch is restrained in the pieces of feature data CDf and CDs obtained from the frequency signals FSf and FSs. For that reason, the determination accuracy of the type of the printing paper PP is increased in the printing apparatus 10E of the fifth embodiment. In the printing apparatus 10E, the printing paper PP is determined based on the features detected from each of the first surface PPf and the second surface PPs of the printing paper PP and thus, a higher determination accuracy can be obtained. According to the configuration, in a case where a medium, for which the feature detected in a printing surface is different from that detected in a rear surface of the printing surface, is used as the printing paper PP, an especially high effect is exhibited. In addition, according to the printing apparatus 10E of the fifth embodiment, the scanning unit 20E (first surface scanning unit 20Ea and second surface scanning unit 20Eb), the transport device 12, and a medium determination device realized in the printing apparatus 10E, it is possible to exhibit various working effects described in the respective embodiments.

Sixth Embodiment

Figure 20B:
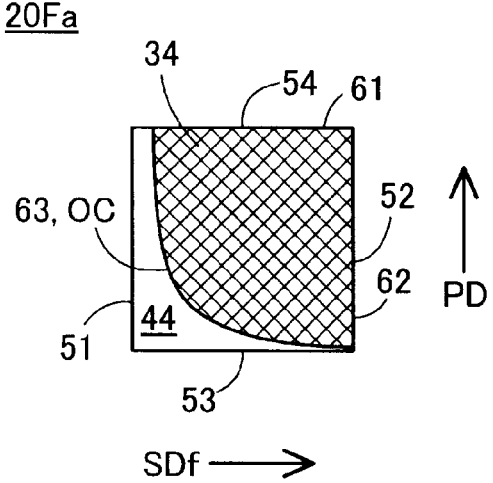
FIG. 20B is a schematic diagram illustrating a direction of a mask opening of the sixth embodiment.
Figure 20C:
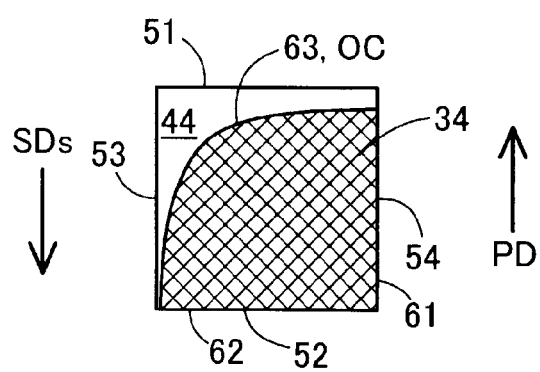
FIG. 20C is a schematic diagram illustrating another direction of the mask opening of the sixth embodiment.

A schematic configuration of a printing apparatus 10F as a sixth embodiment of the invention will be described with reference to FIG. 20A to FIG. 20C. FIG. 20A is a perspective view schematically illustrating a portion of a region, which is extracted and includes a printing head unit 13F and a scanning unit 20F, in the printing apparatus 10F of the sixth embodiment. FIG. 20B and FIG. 20C are schematic diagrams that respectively indicate directions or orientations of the mask openings 44 of two scanning units 20Fa and 20Fb included in the scanning unit 20F. A configuration of the printing apparatus 10F of the sixth embodiment is almost the same as that of the printing apparatus 10E (FIG. 17) of the fifth embodiment except for matters which will be described in the following.

The printing apparatus 10F (FIG. 20A) of the sixth embodiment is so called a serial printer and the printing head unit 13F ejects ink dots onto the printing paper PP under the control of the control unit 11 while reciprocating in a direction intersecting with the transporting direction PD of the printing paper PP. In the printing apparatus 10F, the main scanning direction MD which is a moving direction of the printing head unit 13F is a direction orthogonal to the transporting direction PD which is a sub-scanning direction. The printing apparatus 10F includes a rail 13r installed along the main scanning direction MD above the transport path of the printing paper PP. The printing head unit 13F is guided by the rail 13r and is moved by a rotation driving force of a motor (not illustrated) in the main scanning direction MD.

The scanning unit 20F of the sixth embodiment includes a first surface scanning unit 20Fa that scans the first surface PPf of the printing paper PP and a second surface scanning unit 20Fb that scans the second surface PPs. The configuration of the second surface scanning unit 20Fb is almost the same as that of the second surface scanning unit 20Eb of the fifth embodiment (FIG. 20A and FIG. 20C). A configuration of the first surface scanning unit 20Fa is almost the same as that of the first surface scanning unit 20Ea of the fifth embodiment except for matters which will be described in the following.

The first surface scanning unit 20Fa of the sixth embodiment is attached to the printing head unit 13F and is moved together with the printing head unit 13F in the main scanning direction MD (FIG. 20A). The first surface scanning unit 20Fa scans the first surface PPf of the printing paper PP while the printing head unit 13F is moved. For that reason, the scanning direction SDf of the first surface scanning unit 20Fa is a direction along the main scanning direction MD. However, the scanning direction SDf may also be any direction along the main scanning direction MD. In the first surface scanning unit 20Fa, the mask opening 44 is provided in such a way that the direction of the contour curve OC becomes the same direction as that described in the first embodiment with respect to the scanning direction SDf along the main scanning direction MD (FIG. 20B). That is, in the sixth embodiment, the mask opening 44 of the first surface scanning unit 20Fa is disposed at an angle rotated by 90°, with respect to the mask opening 44 (FIG. 20C) of the second surface scanning unit 20Fb, in a plane parallel to the surface of the printing paper PP which is a scanning target surface.

The printing apparatus 10F executes the medium determination processing in a flow similar to that described in the fifth embodiment (FIG. 19). However, processing contents of Step S10 is different from that of the fifth embodiment as in the following. In Step S10, the control unit 11 separately causes the first surface scanning unit 20Fa and the second surface scanning unit 20Fb to execute scanning of the printing paper PP. The control unit 11 moves the printing head unit 13F in any of the main scanning directions MD in a state where the printing paper PP is stopped and causes the first surface scanning unit 20Fa to scan the first surface PPf of the printing paper PP. The control unit 11 causes the second surface scanning unit 20Fb to scan the second surface PPs of the printing paper PP while the printing paper PP is moved in the transporting direction PD, similar to matters described in the fifth embodiment. By two scanning processing described above, the control unit 11 acquires the first surface feature data CDf and the second surface feature data CDs (Step S20). Thus, the surface scanning unit 20Fa scans during a main scan operation and the surface scanning unit 20Fb scans during a sub-scan operation.

Figure 21:
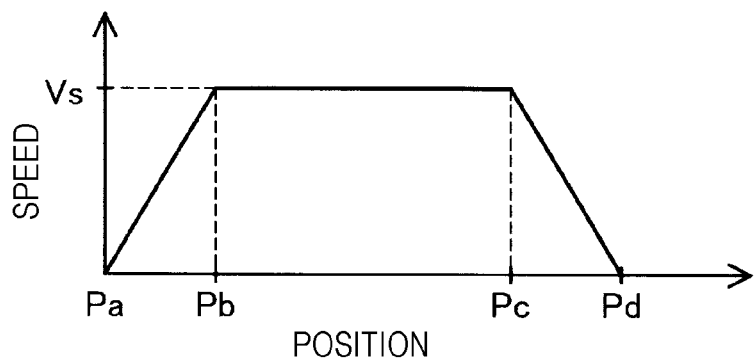
FIG. 21 is a graph illustrating an example of speed control of a printing head.

FIG. 21 is a graph illustrating an example of speed control or of controlling the speed of the printing head unit 13F when scanning by the first surface scanning unit 20Fa is executed. In FIG. 21, a graph indicating a relationship between a position of the first surface scanning unit 20Fa in the scanning direction SDf and a speed Vs of the first surface scanning unit 20Fa is illustrated. The control unit 11 preferably moves the printing head unit 13F and causes the first surface scanning unit 20Fa to scan the first surface PPf of the printing paper PP as in the following, in processing of Step S10 described above.

The control unit 11 accelerates the printing head unit 13F from a stop state to a predetermined speed Vs (from position Pa to position Pb). The control unit 11 causes the printing head unit 13F to move in a predetermined section (from position Pb to position Pc) at a substantially constant speed Vs and then, stops the printing head unit 13F again (position Pd). The control unit 11 causes the first surface scanning unit 20Fa to scan the first surface PPf of the printing paper PP while the printing head unit 13 is moving at a constant speed. Thus, the first surface feature data CDf can be acquired more accurately. A moving distance of the printing head unit 13F between the positions Pb to Pc may be a range, for example, from several mm to several tens of mm or more. The moving distance may be close to a width of the medium.

As described above, also in the medium determination device realized in the printing apparatus 10F of the sixth embodiment, it is possible to acquire the first surface feature data CDf and the second surface feature data CDs similar to matters described in the fifth embodiment and to increase the determination accuracy of the type of the printing paper PP. In addition, according to the printing apparatus 10F of the sixth embodiment, the scanning unit 20F (first surface scanning unit 20Fa and second surface scanning unit 20Fb), the transport device 12, and the medium determination device realized in the printing apparatus 10F, various working effects described in the respective embodiments can be exhibited.

Seventh Embodiment

Figure 22B:
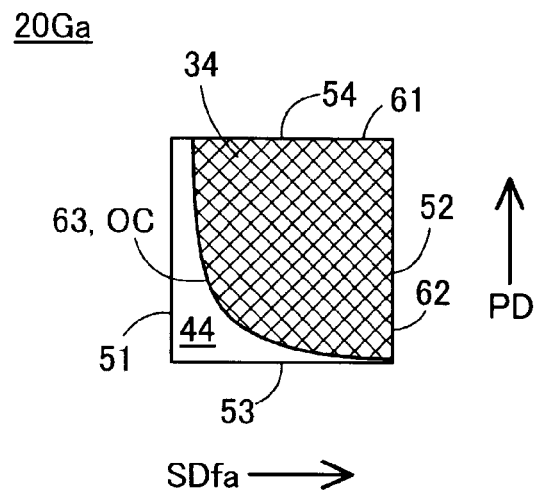
FIG. 22B is a schematic diagram illustrating a direction of a mask opening of the seventh embodiment.
Figure 22C:
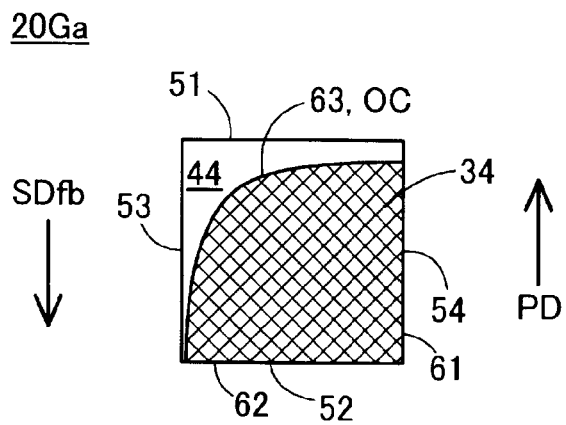
FIG. 22C is a schematic diagram illustrating another direction of the mask opening of the seventh embodiment.
Figure 22D:
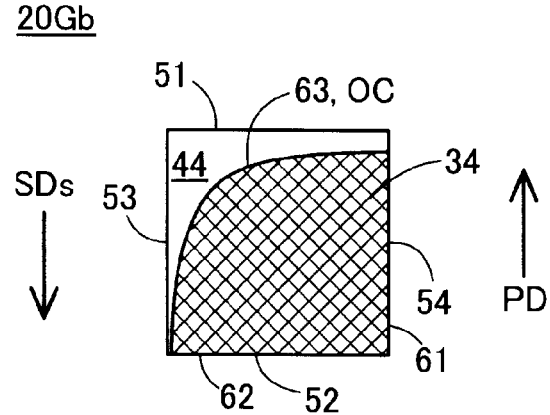
FIG. 22D is a schematic diagram illustrating another direction of the mask opening of the seventh embodiment.

A schematic configuration of a printing apparatus 10G as a seventh embodiment of the invention will be described with reference to FIG. 22A to FIG. 22D. FIG. 22A is a perspective view schematically illustrating a portion of a region, which is extracted and includes a printing head unit 13F and a scanning unit 20G of in the printing apparatus 10G of the seventh embodiment. FIG. 22B to FIG. 22D are schematic diagrams that respectively indicate directions of the mask openings 44 of two scanning units 20Ga and 20Gb included in the scanning unit 20G. A configuration of the printing apparatus 10G of the seventh embodiment is almost the same as that of the printing apparatus 10F of the sixth embodiment except for matters which will be described in the following.

The scanning unit 20G of the seventh embodiment includes the first surface scanning unit 20Ga that scans the first surface PPf of the printing paper PP and the second surface scanning unit 20Gb that scans the second surface PPs of the printing paper PP (FIG. 22A). The configuration of the second surface scanning unit 20Gb of the seventh embodiment is almost the same as the configuration (FIG. 20A and FIG. 20C) of the second surface scanning unit 20Fb of the sixth embodiment (FIG. 22A and FIG. 22D). A configuration of the first surface scanning unit 20Ga of the seventh embodiment is almost the same as the configuration of the first surface scanning unit 20Fa of the sixth embodiment except for matters which will be described in the following.

The first surface scanning unit 20Ga of the seventh embodiment includes a rotation driving unit 26. The rotation driving unit 26 rotates a direction of the mask opening 44 as indicated by an arrow R in a plane parallel to the first surface PPf of the printing paper PP, which is a scanning target, under control of the control unit 11. The rotation driving unit 26 is configured by, for example, a stepping motor or a solenoid. The first surface scanning unit 20Ga changes the direction of the mask opening 44 and executes scanning in two directions including the first direction SDfa and the second direction SDfb, which are described in the following.

The control unit 11 causes the first surface scanning unit 20Ga to execute scanning in the first direction SDfa while the printing head unit 13F is moving in the main scanning direction MD, in a state where the printing paper PP is stopped. For that reason, the first direction SDfa is a direction along the main scanning direction MD. However, the first direction SDfa may be any direction along the main scanning direction MD. Prior to causing the first surface scanning unit 20Ga to start scanning in the first direction SDfa, the control unit 11 sets the direction of the mask opening 44 by causing the driving unit 26 to rotate the mask opening in such a way that the direction of the contour curve OC with respect to the first direction SDfa becomes the direction described in the first embodiment (FIG. 22B). In this case, the direction of the mask opening 44 is the same direction as the mask opening 44 of the first surface scanning unit 20Fa of the sixth embodiment (FIG. 20B).

The control unit 11 causes the first surface scanning unit 20Ga to execute scanning in the second direction SDfb while the printing paper PP is transported in the transporting direction PD in a state where the printing head unit 13F is stopped at a predetermined position. The second direction SDfb is a direction along the transporting direction PD which is the sub-scanning direction and a direction orthogonal to the main scanning direction MD and the first direction SDfa. Prior to causing the first surface scanning unit 20Ga to start scanning in the second direction SDfb, the control unit 11 sets the direction of the mask opening 44 by driving unit 26 to rotate the mask opening in such a way that the direction of the contour curve OC with respect to the second direction SDfb becomes the direction described in the first embodiment (FIG. 22C) if necessary. The control unit 11 rotates the mask opening 44 from a state where, scanning is performed in the first direction SDfa, by 90°. The direction of the mask opening 44 when scanning is performed in the second direction SDfb is the same as that of the mask opening 44 of the first surface scanning unit 20Ea of the fifth embodiment (FIG. 18B).

The printing apparatus 10G executes the medium determination processing in a flow similar to that described in the fifth embodiment (FIG. 19). In Step S10, the control unit 11 causes the first surface scanning unit 20Ga to execute scanning in the first direction SDfa and scanning in the second direction SDfb as described above. The control unit 11 causes the second surface scanning unit 20Gb to execute scanning the second surface PPs of the printing paper PP in the scanning direction SDs. Scanning by the first surface scanning unit 20Ga in the second direction SDfb is efficient when executed in parallel with scanning by the second surface scanning unit 20Gb in the second direction SDfb.

In Step S20, the control unit 11 acquires three types of feature data. The control unit 11 acquires two types of first surface feature data CDf and one type of second surface feature data CDs in total. The control unit 11 acquires the first feature data and the second feature data as the first surface feature data CDf from the first surface scanning unit 20Ga. The first feature data is a piece of feature data obtained from a frequency signal FSf obtained by being subjected to scanning by the first surface scanning unit 20Ga in the first direction SDfa. The second feature data is a piece of feature data obtained by being subjected to scanning by the first surface scanning unit 20Ga in the second direction SDfb. The control unit 11 acquires the second surface feature data CDs from the second surface scanning unit 20Gb.

In Step S30, the control unit 11 executes collation processing for each of three types of feature data described above. Here, first collation data corresponding to the first feature data and second collation data corresponding to the second feature data are stored in the master data storing unit 27 of the printing apparatus 10G as the first surface collation data VDf (not illustrated). In the first surface collation processing of Step S30, the control unit 11 collates the first feature data with the first collation data and also collates the second feature data with the second collation data. In Step S40, processing according to the result of the collation processing for each of three types of feature data is executed similarly to matters described in the fifth embodiment.

As described above, in the medium determination device realized or embodied in the printing apparatus 10G of the seventh embodiment, three types of feature data are detected by the scanning unit 20G and the determination of the type of the printing paper PP is performed using the three types of feature data. For that reason, the determination accuracy of the printing paper PP is further increased compared to other embodiments described above. In addition, according to the printing apparatus 10G, the scanning unit 20G (first surface scanning unit 20Ga and second surface scanning unit 20Gb), the transport device 12, and the medium determination device in the seventh embodiment, various working effects described in the respective embodiments described above can be exhibited.

Eighth Embodiment

Figure 23A:
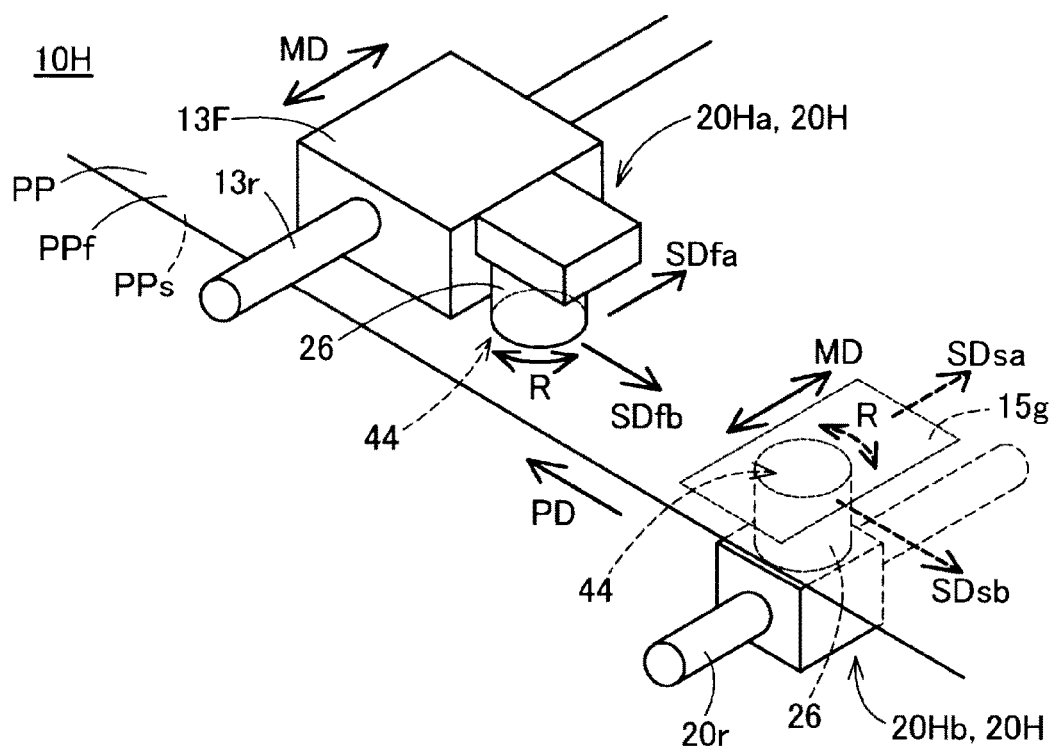
FIG. 23A is a perspective view schematically illustrating a region including a scanning unit of a printing apparatus in an eighth embodiment.
Figure 23B:
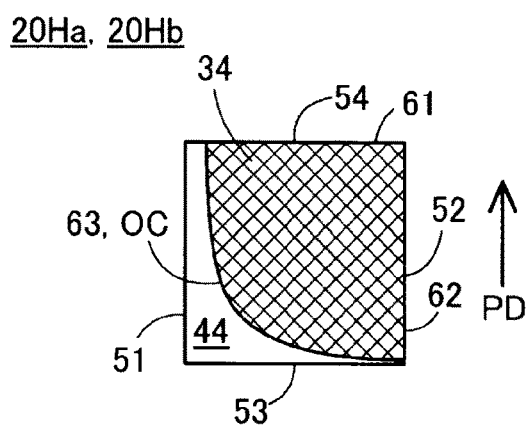
FIG. 23B is a schematic diagram illustrating a direction of a mask opening of the eighth embodiment.
Figure 23C:
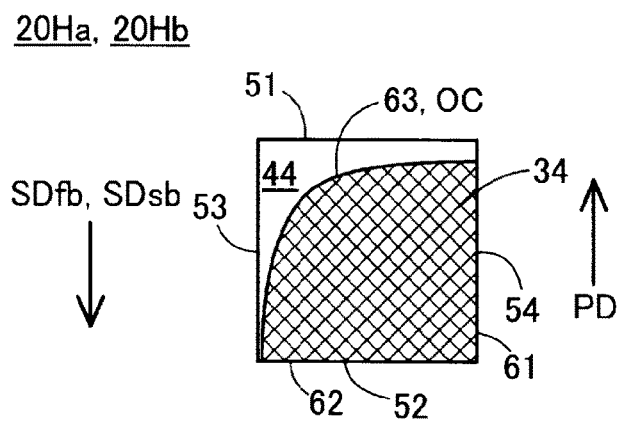
FIG. 23C is a schematic diagram illustrating another direction of the mask opening of the eighth embodiment.

A schematic configuration of a printing apparatus 10H as an eighth embodiment of the invention will be described with reference to FIG. 23A to FIG. 23C. FIG. 23A is a perspective view schematically illustrating a portion of a region, which is extracted and includes a printing head unit 13F and a scanning unit 20H, in the printing apparatus 10H of the eighth embodiment. FIG. 23B and FIG. 23C are schematic diagrams that respectively indicate directions of the mask openings 44 of two scanning units 20Ha and 20Hb included in the scanning unit 20H. A configuration of the printing apparatus 10H of the eighth embodiment is almost the same as that of the printing apparatus 10G of the seventh embodiment except for matters which will be described in the following.

The scanning unit 20H of the eighth embodiment includes a first surface scanning unit 20Ha that scans the first surface PPf of the printing paper PP and a second surface scanning unit 20Hb that scans the second surface PPs of the printing paper PP. A configuration of the first surface scanning unit 20Ha of the eighth embodiment is almost the same as the configuration of the first surface scanning unit 20Ga (FIG. 22A, FIG. 22B, and FIG. 22C) of the seventh embodiment (FIG. 23A, FIG. 23B, and FIG. 23C). A configuration of the second surface scanning unit 20Hb of the eighth embodiment is almost the same as that of the second surface scanning unit 20Gb of the seventh embodiment except for matters which will be described in the following.

The second surface scanning unit 20Hb moves in a direction intersecting the transporting direction PD within a groove 15g (illustrated by a broken line) provided inside the support base 15 (FIG. 23A). A rail 20r installed along the main scanning direction MD is provided within the groove 15g of the support base 15. The second surface scanning unit 20Hb is guided by the rail 20r and moved along the main scanning direction MD by a driving force of a motor (not illustrated). A moving range of the second surface scanning unit 20Hb may be set to be within a range, for example, from several mm to several tens of mm or more.

The second surface scanning unit 20Hb includes the rotation driving unit 26 similar to the first surface scanning unit 20Ha. The rotation driving unit 26 rotates a direction of the mask opening 44 of the second surface scanning unit 20Hb in a plane parallel to the second surface PPs of the printing paper PP, which is a scanning target, under control of the control unit 11. The rotation driving unit 26 is configured by, for example, a stepping motor or a solenoid. The second surface scanning unit 20Hb changes the direction of the mask opening 44 and executes scanning in two directions including the third direction SDsa and the fourth direction SDsb to be described in the following.

The control unit 11 moves the second surface scanning unit 20Hb along the main scanning direction MD in a state where the printing paper PP is stopped. During the movement of the second surface scanning unit 20Hb, the control unit 11 causes the second surface scanning unit 20Hb to execute scanning in the third direction SDsa. The third direction SDsa is a direction along the main scanning direction MD and is the same direction as the first direction SDfa which is one of the scanning directions of the first surface scanning unit 20Ha. Otherwise, any direction may be a scanning direction by the second surface scanning unit 20Hb as long as the scanning direction is along the main scanning direction MD. Thus, the third direction SDsa for scanning may be different from the first direction SDfa. Prior to causing the second surface scanning unit 20Hb to start scanning in the third direction SDsa, the control unit 11 sets the direction of the mask opening 44 with the rotation driving unit 26 to rotate the mask opening in such a way that the direction of the contour curve OC with respect to the third direction SDsa becomes the direction described in the first embodiment (FIG. 23B). The direction of the mask opening 44 of the second surface scanning unit 20Hb when scanning is performed in the third direction SDsa is the same direction as the mask opening 44 of the first surface scanning unit 20Ha when scanning is performed in the first direction SDfa.

The control unit 11 transports the printing paper PP in the transporting direction PD in a state where the second surface scanning unit 20Hb is stopped at a predetermined position. The control unit 11 causes the second surface scanning unit 20Hb to execute scanning in the fourth direction SDSb while the printing paper PP is transported. The fourth direction SDsb is the same direction as the second direction SDfb which is one of the scanning directions of the first surface scanning unit 20Ha and is a direction along the transporting direction PD which is the sub-scanning direction. The fourth direction SDsb is also a direction orthogonal to the main scanning direction MD and the third direction SDsa. Prior to causing the second surface scanning unit 20Hb to start scanning in the fourth direction SDsb, the control unit 11 sets the direction of the mask opening 44 using the rotation driving unit 26 to rotate the mask opening in such a way that the direction of the contour curve OC with respect to the fourth direction SDsb becomes the direction described in the first embodiment (FIG. 23C). The control unit 11 rotates the mask opening 44 by 90° from the state where scanning in the third direction SDsa described above is performed. The direction of the mask opening 44 of the second surface scanning unit 20Hb when scanning in the fourth direction SDsb is performed is the same direction as that of the mask opening 44 of the first surface scanning unit 20Ha when scanning in the second direction SDfb is performed.

The printing apparatus 10H executes the medium determination processing in a flow similar to that described in the fifth embodiment (FIG. 19). In Step S10, the control unit 11 causes the first surface scanning unit 20Ha to execute scanning in the first direction SDfa and scanning in the second direction SDfb. The control unit 11 causes the second surface scanning unit 20Hb to execute scanning in the third direction SDsa and scanning in the fourth direction SDsb. It is efficient to perform scanning by the first surface scanning unit 20Ha in the first direction SDfa in parallel with scanning by the second surface scanning unit 20Hb in the third direction SDsa. Similarly, it is efficient to perform scanning by the first surface scanning unit 20Ha in the second direction SDfb in parallel with scanning by the second surface scanning unit 20Hb in the fourth direction SDsb.

In Step S20, the control unit 11 acquires four types of feature data that includes two types of first surface feature data CDf and two types of second surface feature data CDs. The control unit 11 acquires third feature data and fourth feature data from the second surface scanning unit 20Hb as the second surface feature data CDs, in addition to the first feature data and the second feature data obtained from the first surface scanning unit 20Ha. The third feature data is a piece of feature data obtained from the frequency signal FSf obtained by being subjected to scanning by the second surface scanning unit 20Hb in the third direction SDsa. The fourth feature data is a piece of feature data obtained by being subjected to scanning by the second surface scanning unit 20Hb in the fourth direction SDsb.

In Step S30, the control unit 11 executes collation processing for each of the four types of feature data described above. Here, third collation data corresponding to the third feature data and fourth collation data corresponding to the fourth feature data, as second surface collation data VDs, are stored in the master data storing unit 27 of the printing apparatus 10H, in addition to the first collation data and the second collation data which are first surface collation data VDf (not illustrated). In first surface collation processing of Step S30, the control unit 11 collates the first feature data with the first collation data and also collates the second feature data with the second collation data. In second surface collation processing of Step S30, the control unit 11 collates the third feature data with the third collation data and also collates the fourth feature data with the fourth collation data. In Step S40, processing according to the result of the collation processing for each of four types of feature data is executed similarly to matters described in the fifth Embodiment.

As described above, in the medium determination device realized in the printing apparatus 10H of the eighth embodiment, four types of feature data are detected by the scanning unit 20H and the determination of the type of the printing paper PP is performed using the four types of feature data. For that reason, the determination accuracy of the printing paper PP is further increased compared to other embodiments described above. In addition, according to the printing apparatus 10H, the scanning unit 20H (first surface scanning unit 20Ha and second surface scanning unit 20Hb), the transport device 12, and the medium determination device in the eighth embodiment, various working effects described in the respective embodiments described above can be exhibited.

Ninth Embodiment

Figure 24A:
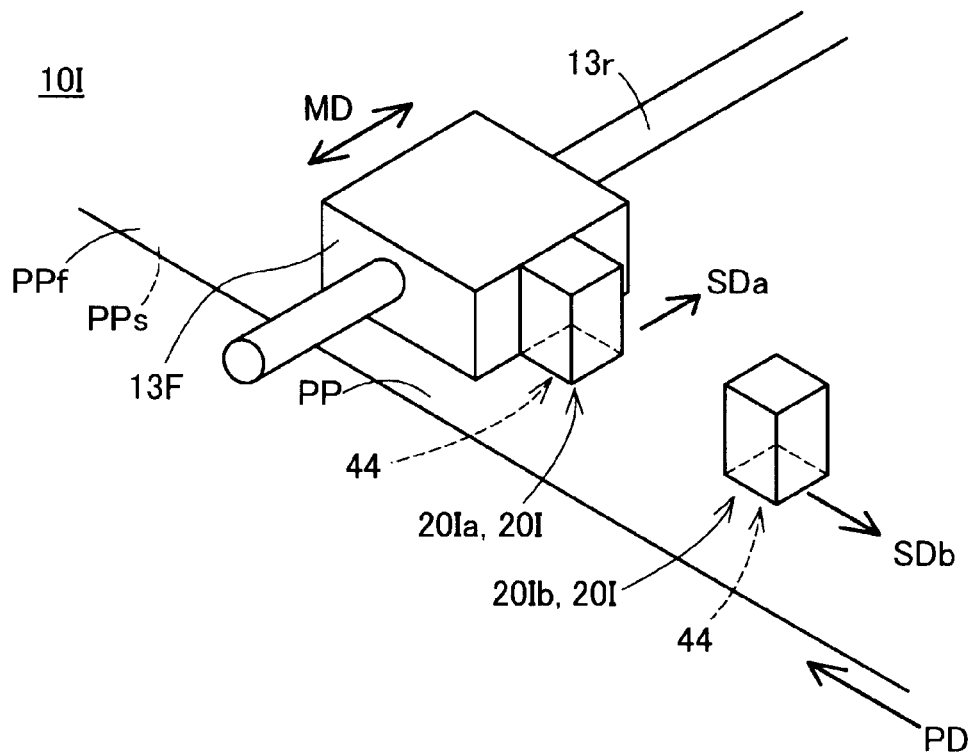
FIG. 24A is a perspective view schematically illustrating a region including a scanning unit of a printing apparatus in a ninth embodiment.
Figure 24B:
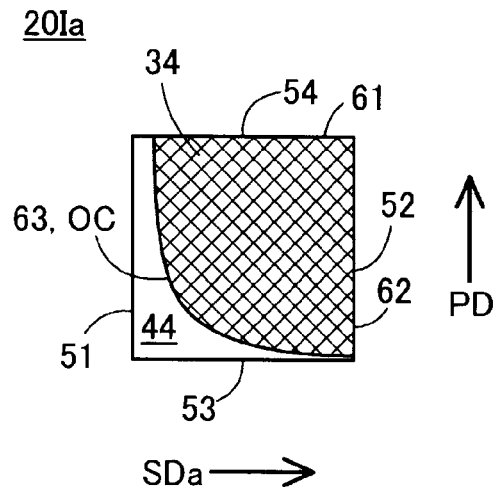
FIG. 24B is a schematic diagram illustrating a direction of a mask opening of the ninth embodiment.
Figure 24C:
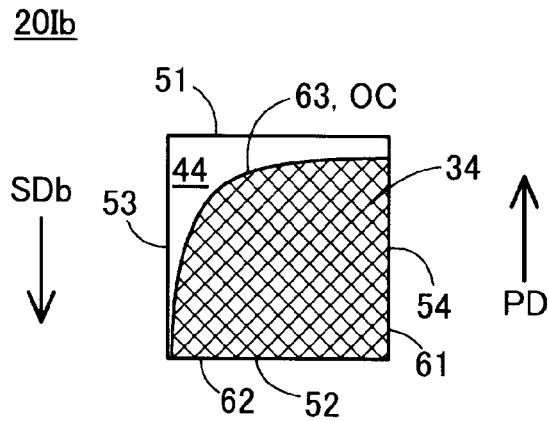
FIG. 24C is a schematic diagram illustrating another direction of the mask opening of the ninth embodiment.

A schematic configuration of a printing apparatus 10I as a ninth embodiment of the invention will be described with reference to FIG. 24A to FIG. 24C. FIG. 24A is a perspective view schematically illustrating a portion of a region, which is extracted and includes a printing head unit 13F and a scanning unit 20I, in the printing apparatus 10I of the ninth embodiment. FIG. 24B and FIG. 24C are schematic diagrams that respectively indicate directions of the mask openings 44 of two scanning units 20Ia and 20Ib included in the scanning unit 20I. A configuration of the printing apparatus 10I of the ninth embodiment is almost the same as that of the printing apparatus 10F of the sixth embodiment except for matters which will be described in the following.

The scanning unit 20I of the ninth embodiment includes a first direction scanning unit 20Ia and a second direction scanning unit 20Ib. The printing apparatus 10I scans the first surface PPf of the printing paper PP by the first direction scanning unit 20Ia and the second direction scanning unit 20Ib in two directions including the first scanning direction SDa and the second scanning direction SDb.

The first direction scanning unit 20Ia has a configuration which is almost the same as that of the first surface scanning unit 20Fa (FIG. 20A and FIG. 20B) of the sixth embodiment and is attached to the printing head unit 13F (FIG. 24A and FIG. 24B). The first direction scanning unit 20Ia scans the first surface PPf of the printing paper PP in the first scanning direction SDa along the main scanning direction MD when the printing paper PP is stopped. The first direction scanning unit 20Ia may be any direction along the main scanning direction MD.

The second direction scanning unit 20Ib has a configuration which is almost the same as that of the second surface scanning unit 20Fb (FIG. 20A and FIG. 20C) of the sixth embodiment except that the second direction scanning unit 20Ib is not installed inside of the support base 15. Rather, the second direction scanning unit 20Ib is installed above the transport path of the printing paper PP (FIG. 24A and FIG. 24B). When the printing paper PP is transported in the transporting direction PD, the second direction scanning unit 20Ib scans the first surface PPf of the printing paper PP in the second scanning direction SDb along the transporting direction PD which is the sub-scanning direction.

The printing apparatus 10I executes the medium determination processing in a flow similar to that described in the fifth embodiment (FIG. 19). In Step S10, the control unit 11 causes the first surface scanning unit 20Ia to execute scanning in the first scanning direction SDa described above. The control unit 11 causes the second surface scanning unit 20Ib to execute scanning in the second scanning direction SDb described above.

In Step S20, the control unit 11 acquires a group of frequency signals output by the first direction scanning unit 20Ia as first direction feature data at a predetermined period. Similarly, the control unit 11 acquires a group of frequency signals output by the second direction scanning unit 20Ib as second direction feature data at a predetermined period.

In Step S30, the control unit 11 executes collation processing regarding each of first direction feature data and second direction feature data. First direction collation data corresponding to the first direction feature data and second direction collation data corresponding to the second direction feature data are stored, as master data for collation, in the master data storing unit 27 of the printing apparatus 10I (not illustrated). In Step S30, the control unit 11 collates the first direction feature data with the first direction collation data and also collates the second direction feature data with the second direction collation data. In Step S40, processing according to the result of the collation processing for each of the first direction feature data and the second direction feature data is executed similarly to matters described in the fifth embodiment.

In each of the frequency signals output by the first direction scanning unit 20Ia and the second direction scanning unit 20Ib of the ninth embodiment, the occurrence of the notch is restrained due to a shape of the mask opening 44 similarly as described in the first embodiment. Accordingly, insufficient or missing of information due to the occurrence of the notch is restrained in the first direction feature data and the second direction feature data obtained from the frequency signals. Thus, the determination accuracy of the type of the printing paper PP is increased in the printing apparatus 10I. In the printing apparatus 10I, at least the type of the printing paper PP can be determined based on the feature detected by scanning in two directions on the first surface PPf of the printing paper PP and thus, it is possible to obtain a higher determination accuracy. According to the configuration, in a case where a medium having a feature reflected or contained in information detected from the printing surface side is used as the printing paper PP, an especially high effect is exhibited. In addition, according to the printing apparatus 10I of the ninth embodiment, the scanning unit 20I (first surface scanning unit 20Ia and second surface scanning unit 20Ib), the transport device 12, and a medium determination device realized in the printing apparatus 10I, various working effects described in the respective embodiments can be exhibited.

Tenth Embodiment

Figure 25A:
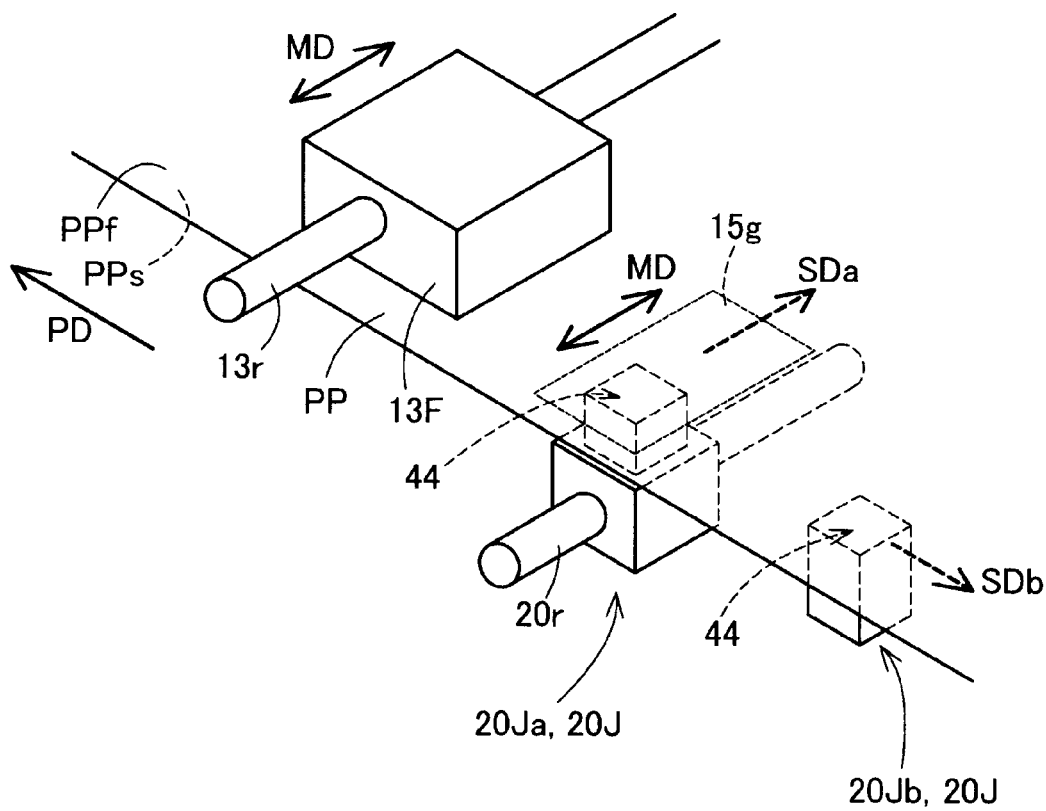
FIG. 25A is a perspective view schematically illustrating a region including a scanning unit of a printing apparatus in a tenth embodiment.
Figure 25B:
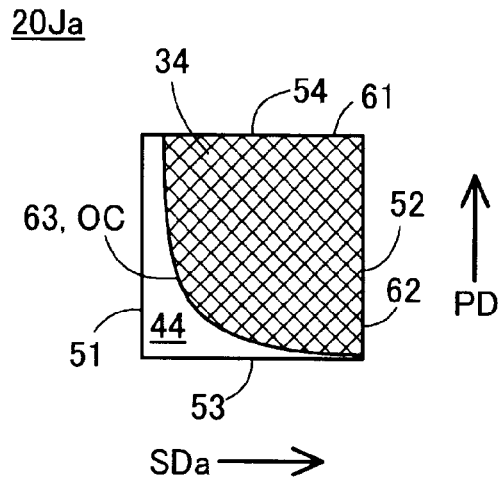
FIG. 25B is a schematic diagram illustrating a direction of a mask opening of the tenth embodiment.
Figure 25C:
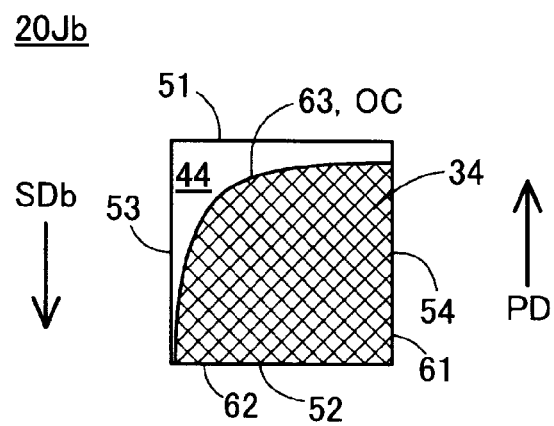
FIG. 25C is a schematic diagram illustrating another direction of the mask opening of the tenth embodiment.

A schematic configuration of a printing apparatus 10J as a tenth embodiment of the invention will be described with reference to FIG. 25A to FIG. 25C. FIG. 25A is a perspective view schematically illustrating a portion of a region, which is extracted and includes a printing head unit 13F and a scanning unit 20J, in the printing apparatus 10J of the tenth embodiment. FIG. 25B and FIG. 25C are schematic diagrams that respectively indicate directions or orientations of the mask openings 44 of first direction scanning unit 20Ja and the second direction scanning unit 20Jb included in the scanning unit 20J. A configuration of the printing apparatus 10J of the tenth embodiment is almost the same as that of the printing apparatus 10I of the ninth embodiment except for matters which will be described in the following. The printing apparatus 10J may also be configured as a line printer including the printing head unit 13E (FIG. 18A) described in the fifth embodiment, instead of the printing head unit 13F.

The scanning unit 20J of the tenth embodiment includes a first direction scanning unit 20Ja and a second direction scanning unit 20Jb (FIG. 25A). Each of the first direction scanning unit 20Ja and the second direction scanning unit 20Jb scans the second surface PPs of the printing paper PP in two directions of the first scanning direction SDa and the second scanning direction SDb.

The first direction scanning unit 20Ja is moved along the main scanning direction MD by a moving mechanism having a configuration which is almost the same as that of a moving mechanism (FIG. 23A) of the second surface scanning unit 20Hb of the eighth embodiment. When the printing paper PP is stationary, the first direction scanning unit 20Ja scans the second surface PPs of the printing paper PP in the first scanning direction SDa along the main scanning direction MD (FIG. 25A). However, the first scanning direction SDa may be any direction along the main scanning direction MD. The mask opening 44 of the first direction scanning unit 20Ja may be provided in such a way that the direction of the contour curve OC with respect to the first scanning direction SDa becomes the same direction as that described in the first embodiment (FIG. 25B).

A configuration of the second direction scanning unit 20Jb is almost the same as the configuration of the second surface scanning unit 20Eb (FIG. 18A and FIG. 18B) of the fifth embodiment (FIG. 25A and FIG. 25C). When the printing paper PP is transported in the transporting direction PD, the second direction scanning unit 20Jb scans the second surface PPs of the printing paper PP in the second scanning direction SDb along the transporting direction PD.

The control unit 11 of the printing apparatus 10J acquires the first direction feature data and the second direction feature data that represent the feature detected from the second surface PPs side of the printing paper PP from the frequency signals output from the first direction scanning unit 20Ja and the second direction scanning unit 20Jb. The type of the printing paper PP is determined using the first direction feature data and the second direction feature data.

According to the printing apparatus 10J of the tenth embodiment, a determination accuracy of the type of the printing paper PP which is a medium is increased, similarly as in the printing apparatus 10I of the ninth embodiment. In addition, according to the printing apparatus 10J of the tenth embodiment, the scanning unit 20J (first direction scanning unit 20Ja and second direction scanning unit 20Jb), the transport device 12, and a medium determination device realized in the printing apparatus 10J, various working effects described in the respective embodiments can be exhibited.

Eleventh Embodiment

FIG. 26 is a schematic diagram illustrating a configuration of a sorting device 100 as an eleventh embodiment of the invention. The sorting device 100 determines a type of a medium MM, sorts the medium MM by the type, and stores the medium MM. The sorting device 100 includes an accommodation unit 105, a storing unit 110, a transport unit 120, a medium determination device 130, and a transport control unit 140.

The accommodation unit 105 accommodates a plurality of types of media (or medium) MM before being sorted. IN other words, different types of media, which may be randomly stacked, may be placed in the accommodation unit 105. The medium MM may be a cut form formed by cutting the printing paper PP described in respective embodiments and also be a paper sheet, a sheet-like member, a card, a plate-shaped member and the like other than the cut form. As the medium MM, any medium is available as long as feature data of each type of the medium can be detected by optical scanning in the medium determination device 130. The accommodation unit 105 includes a delivery roller 106 that delivers the medium MM one by one to a transport path 121 of the transport unit 120.

The storing unit 110 includes a plurality of storage racks 111. At least a number of storage racks 111 corresponding to the number of types of the medium MM which is a processing target are prepared. In one example, the number of storage racks 111 may correspond to the number of types of media. Alternatively groups of different types of media may be directed to certain racks 111, for example, when the number of media types is greater than the number of storage racks 111. The media MM transported by the transport unit 120 are stored in each of the storage racks 111 by or based on the type of the media MM.

The transport unit 120 includes the transport path 121 connecting the accommodation unit 105 and the storing unit 110. The transport path 121 is configured by a plurality of transport rollers 122 transporting the medium MM. In FIG. 26, the transport path 121 is illustrated by an alternate long and short dash line.

A switching unit 123 is provided on or in or as part of the transport path 121. The transport path 121 branches into a plurality of directions in the switching unit 123 and is or can be connected to each of the storage racks 111 of the storing unit 110. The switching unit 123 includes a roller or a lever for switching a transport destination of the transport path 121. The switching unit 123 drives the roller or the lever under control of the transport control unit 140 and switches the transport destination of the medium MM to any of a plurality of storage racks 111 according to an instruction of the transport control unit 140.

The medium determination device 130 is provided at an upstream side of the switching unit 123 of the transport path 121. The medium determination device 130 has the same configuration as any of the medium determination devices configured in the printing apparatuses 10D to 10J of the fourth embodiment to the tenth embodiment described above. The medium determination device 130 irradiates light toward the surface of the medium MM which is transported in the transport path 121, acquires feature data representing the feature detected from the surface side of the medium MM based on reflected light received through the mask opening 44 (FIG. 3), and determines the type of the medium MM.

The transport control unit 140 is configured by a microcomputer including a CPU and a RAM, and the CPU reads various instructions or programs from the RAM and executes or performs the instructions or programs to perform or accomplish various functions. The transport control unit 140 controls driving of the transport roller 122 to control the transport of the medium MM in the sorting device 100. The transport control unit 140 controls the transport of the medium MM in the medium determination device 130 to be performed in synchronization with scanning of the medium MM in the medium determination device 130.

The transport control unit 140 receives a determination result of the medium determination device 130. The transport control unit 140 controls the switching unit 123 according to the determination result and switches the transport destination of the medium MM to the storage rack 111 corresponding to a determined type reflected in the determination result.

An arrangement conversion unit 125 configured to change the direction of the medium MM may be provided at the downstream side of the medium determination device 130 in the transport path 121. The arrangement conversion unit 125 may also include a bended or curved transport path or a turn table for rotating the medium MM in a horizontal direction. The arrangement conversion unit 125 may also include a transport path in which the medium MM is folded back and transported such that a top surface of the medium MM is replaced with a bottom surface thereof.

In a case where the medium determination device 130 is configured to scan the medium MM in a plurality of directions and detect feature data, it is possible to specify a direction along which the medium MM is transported based on the feature data in each scanning direction. In a case where the medium determination device 130 is configured to scan the first surface PPf and the second surface PPs of the medium MM and detect feature data, it is possible to specify which surface of the medium MM is oriented upward or downward in the arrangement conversion unit 125 during the transport of the medium MM based on pieces of feature data detected from respective surface sides. The transport control unit 140 receives the detection result described above from the medium determination device 130 and changes the direction or orientation of the medium MM to a predetermined direction or orientation according to which the medium MM is to be accommodated in the storing unit 110 based on the detection result. Thus, an accommodation state of the medium MM can be well-balanced in the storing unit 110.

According to the sorting device 100 of the eleventh embodiment, as having been described in the respective embodiment described above, a determination accuracy of the type of the medium MM is increased in the medium determination device 130 and thus, accuracy in sorting by which the media MM is sorted according to type is increased. In addition, according to the medium determination device 130 or the sorting device 100 of the eleventh embodiment, various working effects similar to those described in the respective embodiments described above can be exhibited.

MODIFICATION EXAMPLES

Modification Example 1

An opening shape of an opening portion through which reflected light passes in an optical scanning device is not limited to the shapes of the mask openings 44, 44B, and 44D described in the embodiments described above. The shape of the passing region through which reflected light passes in the optical scanning device may be a shape in which a region, which is in contact with the contour curve OC, can be divided into the minute regions $SQ_1$ to $SQ_n$ having the widths $L_1$ to $L_n$, which are different from one another, described in the first embodiment. The passing region through which reflected light guided to the photosensor 47 passes is preferably a single region which is not separated into a plurality of sub-regions in the scanning direction SD. This is because when two or more passing regions are present in the scanning direction SD, there is a possibility that accuracy of a frequency signal to be obtained is lowered although reflected light reflected on two or more different regions may be received at once.

Modification Example 2

The optical scanning devices 20 and 20D of the respective embodiments scan the printing paper PP being transported as a scanning target at the detection points DPa, DPb, and DP of which positions are fixed on the transport path. In contrast, the optical scanning devices 20 and 20D may be configured in such a way that a position of a light source of the scanning light or an emission angle of the scanning light is moved to allow the printing paper PP which is in a stopped state to be scanned. The optical scanning devices 20 and 20D of the respective embodiments described above can exhibit high effect in scanning of the medium that is relatively moved in a specific scanning direction SD according to the opening shapes of the mask openings 44, 44B, and 44C.

Modification Example 3

In the respective embodiments described above, although the opening shapes of the opening portions 43, 43B, and 43C are specified in the reflection unit 33 using the mask members 34 and 34*a* to 34*d*, the mask members 34 and 34*a* to 34*d* may be omitted. The cross-sectional shapes of the opening portions 43, 43B, and 43C may be configured to have shapes like the opening shapes of the mask openings 44, 44B, and 44C, instead of attaching the mask members 34 and 34*a* to 34*d* to the opening portions 43, 43B, and 43C. In this case, it can be understood that the entirety of a reflected-light passing unit configures the passing region.

Modification Example 4

The photosensor 47 of each of the embodiments described above is not limited to a photodiode and may be configured by another light receiving element. The photosensor 47 may be configured by, for example, a photo transistor.

Modification Example 5

In the respective embodiments described above, the passing region through which the reflected light guided to the photosensor 47 passes is configured by each of the opening regions of the opening portions 43, 43B, and 43C formed on the bottom wall surface 42 of the reflection unit 33. In contrast, the passing region through which the reflected light passes may not be configured by the opening region of the opening portion 43. For example, the passing region may be configured by a region in which light can be reflected in a mirror device that further reflects the reflected light reflected on the medium to be guided to the photosensor 47.

Modification Example 6

In the transport device 12 of the first embodiment described above or the transport devices incorporated into the optical scanning devices including the mask openings 44B and 44C described in the second embodiment and the third embodiment, a configuration for determining the type of the printing paper PP which is the transport medium described with reference to the printing apparatus of the fourth embodiment to the tenth embodiment may be added, in addition to a configuration for acquiring the parameters relating to the transport state of the printing paper PP which is the transport medium. In the printing apparatuses 10D to 10J of the fourth embodiment to the tenth embodiment, the mask opening 44B of the second embodiment or the mask opening 44C of the third embodiment may be applied to the mask opening of the scanning unit or the optical scanning device.

Modification Example 7

In the respective embodiments described above, the optical scanning devices 20 and 20D are incorporated into the printing apparatuses 10 and 10D and scan the printing paper PP as the medium of the scanning target, respectively. In contrast, the optical scanning devices 20 and 20D may be incorporated into apparatuses other than the printing apparatuses 10 and 10D and may scan a medium other than the printing paper PP as the scanning target, respectively. The optical scanning devices 20 and 20D may be incorporated into, for example, a transport path of paper money and may scan paper money as the medium of the scanning target, respectively. In this case, a measurement of a transport speed or transport amount of paper money, a determination of a type of paper money or genuineness of paper money, or the like may be performed based on the frequency signal FS output from the optical scanning devices 20 and 20D.

Modification Example 8

In the respective embodiments described above other than the eleventh embodiment, a strip-shaped printing paper PP is scanned as a medium of a scanning target. In contrast, the medium of the scanning target is not limited to the strip-shaped printing paper PP. The medium may be a cut form which is formed by cutting the printing paper PP described in respective embodiments and also be a paper sheet, a sheet-like member, a card, a plate-shaped member and the like other than the cut form. As the medium, any medium, from which feature data can be detected by scanning with irradiation of light, may be available. In the first embodiment to the fourth embodiment described above, the printing head unit 13 may have a configuration for a line printer similar to that described in the fifth embodiment and may also have a configuration for a serial printer similar to that described in the sixth embodiment.

The printing head unit 13 may also be configured to be able to move in two directions parallel to the surface of the printing paper PP. In a case where the printing head unit is able to be moved in two directions, as in the seventh embodiment or the eighth embodiment described above, the printing head unit can be configured in such a way that a single scanning unit including the rotation driving unit is attached to the printing head or can be configured in such a way that two scanning units of which directions are aligned in two directions, along which the printing heads are able to be moved, respectively.

The configuration described in the specification is not limited as long as a configuration in which the scanning unit and the printing paper PP are relatively movable and the relative movement direction can be coincident with the direction of the scanning unit is available.

Modification Example 9

Each of the scanning units included in the scanning units 20E to 20J of the printing apparatus 10E to 10J of the fifth embodiment to the tenth embodiment described above includes the mask opening 44 described in the first embodiment. In contrast, each of the scanning units of the scanning units 20E to 20J may include the mask opening 44B and 44C (FIG. 12 and FIG. 14) described in the second embodiment and the third embodiment or the mask opening described in the modification example 1. Respective scanning units included in the scanning units 20E to 20J of the respective embodiments may not include the mask openings of the same type in common and may include the mask openings whose types are different from each other.

Modification Example 10

In the fifth embodiment to the ninth embodiment described above, respective scanning units attached to the printing head units 13E and 13F may be provided at locations separated from the printing head units 13E and 13F. In this case, the scanning unit which is described as being moved together with the printing head unit 13F may also be moved by the moving mechanism of the scanning unit described in the eighth embodiment or the tenth embodiment.

Modification Example 11

In the fourth embodiment to the tenth embodiment described above, the scanning directions of the scanning units 20E to 20J are directions along the main scanning direction MD or the sub-scanning direction PD. In contrast, the scanning direction of each of the scanning units 20E to 20J may be a direction different from the main scanning direction MD or the sub-scanning direction PD. For example, in the printing apparatus 10H of the eighth embodiment, the second surface scanning unit 20Hb may be moved in a direction obliquely intersecting the transporting direction PD. Similarly, in the printing apparatus 10J of the tenth embodiment, the first direction scanning unit 20Ja may also be moved in a direction obliquely intersecting the transporting direction PD.

Modification Example 12

In the configuration of the ninth embodiment or the tenth embodiment described above, a configuration in which the printing paper PP, which is cut to be a cut form, is transported may be adopted, the transport of the printing paper PP which is turned upside down may be repeated, and the scanning units 20I and 20J may be caused to scan both surfaces of the printing paper PP. That is, after causing the scanning units 20I and 20J to scan a first surface side of the printing paper PP, the printing paper PP is turned upside down and the scanning units 20I and 20J may be caused to scan a second surface side which is a side opposite to the first surface side of the printing paper PP. In this case, a configuration in which the printing paper PP is automatically turned upside down may be added on the transport path of the transport device 12 and otherwise, the user may also turn the printing paper PP upside down. According to the configuration, scanning is performed on each of both surfaces of the printing paper PP in two directions and four pieces of feature data are detected. Accordingly, determination accuracy of the type of the printing paper PP is increased. A complicated configuration of a scanning unit compared to the seventh embodiment or the eighth embodiment described above is not needed.

The invention is not limited to the embodiments, exemplary examples, and the modification examples described above, and may be realized by various configurations within a range without departing from a gist of the invention. For example, the embodiments, the exemplary examples, and the modification examples corresponding to technical features of the respective aspects of the invention described in the paragraph of the summary of the invention can be appropriately replaced or combined in order to some or all of the problems to be solved described above or achieve some or all of effects described above. The technical features which are not described as essential constitutional elements in the specification can be appropriately deleted.

What is claimed is:

1. An optical scanning device that scans a medium with incoherent scanning light in a scanning direction, the optical scanning device comprising:

a scanning light emission unit that emits the scanning light;

a reflected-light passing unit that includes a passing region through which a portion of reflected light, that is the scanning light reflected by the medium, passes;

a light-reception-signal output unit that receives the reflected light passing through the passing region and outputs a signal representing a temporal change of intensity of the reflected light at a predetermined period; and a signal generation unit that generates a frequency signal of each period at which a fast Fourier transform is performed on the signal output from the light-reception-signal output unit and outputs the frequency signal, wherein an outer peripheral contour line of the passing region includes a contour curve configured with a set of points where coordinates in an orthogonal direction orthogonal to a scanning direction are uniquely determined with respect to the coordinates in the scanning direction, the contour curve renders a curve protruding toward the passing region, and when a region which is in contact with the contour curve in the passing region is divided into a plurality of quadrilateral minute regions whose areas are equivalent to one another and which extend from the contour curve to predetermined coordinate positions in the scanning direction and are continuously arranged in the orthogonal direction, widths of the minute regions in the scanning direction are different for each location in the orthogonal direction, wherein:

when L is set as coordinates in the scanning direction, x is set as coordinates in the orthogonal direction, and A and B are set as arbitrary positive numbers, C is set as an arbitrary real number, and α is set as an arbitrary negative number, the curve rendered by the contour curve is represented as $L = A \cdot (B \cdot x)^\alpha + C$.

2. The optical scanning device according to claim 1, wherein when a is set as an arbitrary positive real number, the curve rendered by the contour curve is represented as, $L = (2 \cdot x)^{-1/a}$.

3. The optical scanning device according to claim 2, wherein the a is a real number greater than or equal to 1 and less than or equal to 3.

4. The optical scanning device according to claim 3, wherein the a is equal to 2.

5. A transport device comprising:

a transport path in which a transport medium is transported in a transporting direction;

a first detection unit and a second detection unit that are configured by the optical scanning device according to claim 4 that scans the transport medium by setting a direction along the transporting direction as a scanning direction;

an operation unit that outputs a parameter relating to a transport state of the transport medium using a first frequency signal which is a frequency signal output from a signal generation unit of the first detection unit and a second frequency signal which is a frequency signal output from the signal generation unit of the second detection unit; and a transport control unit that controls transport of the transport medium in the transport path using the parameter, wherein a first detection point which is a position at which the first detection unit scans the transport medium and a second detection point which is a position at which the second detection unit scans the transport medium are arranged with a predetermined separation distance between the first detection unit and the second detection unit in the transport path in the transporting direction, and the operation unit calculates the parameter using a period difference between a change in the first frequency signal and a change in the second frequency signal and the separation distance.

6. A transport device comprising:

a transport path in which a transport medium is transported in a transporting direction;

a first detection unit and a second detection unit that are configured by the optical scanning device according to claim 3 that scans the transport medium by setting a direction along the transporting direction as a scanning direction;

an operation unit that outputs a parameter relating to a transport state of the transport medium using a first frequency signal which is a frequency signal output from a signal generation unit of the first detection unit and a second frequency signal which is a frequency signal output from the signal generation unit of the second detection unit; and a transport control unit that controls transport of the transport medium in the transport path using the parameter, wherein a first detection point which is a position at which the first detection unit scans the transport medium and a second detection point which is a position at which the second detection unit scans the transport medium are arranged with a predetermined separation distance between the first detection unit and the second detection unit in the transport path in the transporting direction, and the operation unit calculates the parameter using a period difference between a change in the first frequency signal and a change in the second frequency signal and the separation distance.

7. A transport device comprising:

a transport path in which a transport medium is transported in a transporting direction;

a first detection unit and a second detection unit that are configured by the optical scanning device according to claim 2 that scans the transport medium by setting a direction along the transporting direction as a scanning direction;

an operation unit that outputs a parameter relating to a transport state of the transport medium using a first frequency signal which is a frequency signal output from a signal generation unit of the first detection unit and a second frequency signal which is a frequency signal output from the signal generation unit of the second detection unit; and a transport control unit that controls transport of the transport medium in the transport path using the parameter, wherein a first detection point which is a position at which the first detection unit scans the transport medium and a second detection point which is a position at which the second detection unit scans the transport medium are arranged with a predetermined separation distance between the first detection unit and the second detection unit in the transport path in the transporting direction, and the operation unit calculates the parameter using a period difference between a change in the first frequency signal and a change in the second frequency signal and the separation distance.

8. The optical scanning device according to claim 1, wherein the contour curve is a first contour curve, and the outer peripheral contour line further includes a second contour curve which is located at a position opposing the first contour curve so as to sandwich the passing region in the scanning direction and is in a mirror-symmetry with respect to the first contour curve in the scanning direction.

9. The optical scanning device according to claim 8, wherein the outer peripheral contour line further includes
a third contour curve which is located at a position opposing the first contour curve so as to sandwich the passing region in the orthogonal direction and is in a mirror-symmetry with respect to the first contour curve in the orthogonal direction, and
a fourth contour curve which is located at a position opposing the second contour curve so as to sandwich the passing region in the orthogonal direction and is in a mirror-symmetry with respect to the second contour curve in the orthogonal direction.

10. A transport device comprising:
a transport path in which a transport medium is transported in a transporting direction;
a first detection unit and a second detection unit that are configured by the optical scanning device according to claim 8 that scans the transport medium by setting a direction along the transporting direction as a scanning direction;
an operation unit that outputs a parameter relating to a transport state of the transport medium using a first frequency signal which is a frequency signal output from a signal generation unit of the first detection unit and a second frequency signal which is a frequency signal output from the signal generation unit of the second detection unit; and
a transport control unit that controls transport of the transport medium in the transport path using the parameter,
wherein a first detection point which is a position at which the first detection unit scans the transport medium and a second detection point which is a position at which the second detection unit scans the transport medium are arranged with a predetermined separation distance between the first detection unit and the second detection unit in the transport path in the transporting direction, and
the operation unit calculates the parameter using a period difference between a change in the first frequency signal and a change in the second frequency signal and the separation distance.

11. A transport device comprising:
a transport path in which a transport medium is transported in a transporting direction;
a first detection unit and a second detection unit that are configured by the optical scanning device according to claim 1 that scans the transport medium by setting a direction along the transporting direction as a scanning direction;
an operation unit that outputs a parameter relating to a transport state of the transport medium using a first frequency signal which is a frequency signal output from a signal generation unit of the first detection unit and a second frequency signal which is a frequency signal output from the signal generation unit of the second detection unit; and
a transport control unit that controls transport of the transport medium in the transport path using the parameter,
wherein a first detection point which is located at a position at which the first detection unit scans the transport medium and a second detection point which is located at a position at which the second detection unit scans the transport medium are arranged with a predetermined separation distance between the first detection unit and the second detection unit in the transport path in the transporting direction, and
the operation unit calculates the parameter using a period difference between a change in the first frequency signal and a change in the second frequency signal and the separation distance.

12. A feature detection device that detects features of a medium, the feature detection device comprising:
the optical scanning device according to claim 1 that scans the medium, and
a feature data acquisition unit that acquires a group of frequency signals generated at each period as feature data that represents the feature.

13. A medium determination device that determines a type of a medium, the medium determination device comprising:
a scanning unit that scans the medium, is configured by the optical scanning device according to claim 1, and includes a first surface scanning unit and a second surface scanning unit that respectively scan a first surface and a second surface of the medium;
a feature data acquisition unit that acquires a group of frequency signals generated by the first surface scanning unit at each period as first surface feature data and acquires a group of the frequency signals generated by the second surface scanning unit at each period as second surface feature data;
a master data storing unit that stores master data prepared for each type of the medium in advance and including first surface collation data corresponding to the first surface feature data and second surface collation data corresponding to the second surface feature data; and
a determination processing unit that determines the type of the medium by executing first surface collation processing of collating the first surface feature data with the first surface collation data and executing second surface collation processing of collating the second surface feature data with the second surface collation data.

14. The medium determination device according to claim 13,
wherein the first surface scanning unit scans the first surface of the medium in a first direction and a second direction intersecting with the first direction,
the first surface feature data acquired by the feature data acquisition unit includes first feature data generated when the first surface scanning unit scans the medium in the first direction and second feature data generated when the first surface scanning unit scans the medium in the second direction,
the first surface collation data stored by the master data storing unit includes first collation data corresponding to the first feature data and second collation data corresponding to the second feature data, and
the determination processing unit collates the first feature data with the first collation data and collates the second feature data with the second collation data in first surface collation processing.

15. The medium determination device according to claim 14,
wherein the second surface scanning unit scans the second surface of the medium in a third direction and a fourth direction intersecting with the third direction,
the second surface feature data acquired by the feature data acquisition unit includes third feature data generated when the second surface scanning unit scans the medium in the third direction and fourth feature data generated when the second surface scanning unit scans the medium in the fourth direction, the second surface collation data stored by the master data storing unit includes third collation data corresponding to the third feature data and fourth collation data corresponding to the fourth feature data, and the determination processing unit collates the third feature data with the third collation data and collates the fourth feature data with the fourth collation data in second surface collation processing.

16. A sorting device that sorts a medium by each type, the sorting device comprising:

a plurality of storing units each store the medium for each type of the medium;

a transport unit that includes a transport path in which the medium is transported and a switching unit switching a connection destination of the transport path to any of the plurality of storing units;

the medium determination device according to claim 13 that determines the type of the medium transported by the transport unit; and a transport control unit that controls the switching unit according to the determination result of the medium determination device and switches a transport destination of the medium.

17. A medium determination device that determines a type of a medium, the medium determination device comprising:

a scanning unit that is configured by the optical scanning device according to claim 1, scans the medium, and includes a first direction scanning unit scanning the medium in a first scanning direction and a second direction scanning unit scanning the medium in a second scanning direction intersecting with the first scanning direction;

a feature data acquisition unit that acquires a group of frequency signals generated by the first direction scanning unit at each period as first direction feature data and acquires a group of the frequency signals generated by the second direction scanning unit at each period as second direction feature data;

a master data storing unit that stores master data prepared for each type of the medium in advance and includes first direction collation data corresponding to the first direction feature data and second direction collation data corresponding to the second direction feature data; and a determination processing unit that determines the type of the medium by executing collation processing of collating the first direction feature data with the first direction collation data and collating the second direction feature data with the second direction collation data.

18. A medium scanning method, comprising:

scanning the medium by emitting incoherent scanning light in a scanning direction;

causing a portion of reflected light that is the scanning light reflected by the medium to pass through a passing region;

receiving the reflected light passed through the passing region and outputting a signal representing a temporal change of intensity of the reflected light at a predetermined period; and generating a frequency signal of each period at which the fast Fourier transform is performed on the signal and outputting the frequency signal, wherein an outer peripheral contour line of the passing region includes a contour curve configured with a set of points where coordinates in an orthogonal direction orthogonal to a scanning direction are uniquely determined with respect to the coordinates in the scanning direction, the contour curve renders a curve protruding toward the passing region, and when a region which is in contact with the contour curve in the passing region is divided into a plurality of quadrilateral minute regions of which areas are equivalent to one another and which extend from the contour curve to a predetermined coordinate position in the scanning direction and are continuously arranged in the orthogonal direction, widths of the minute regions in the scanning direction are different for each location in the orthogonal direction, wherein:

when L is set as coordinates in the scanning direction, x is set as coordinates in the orthogonal direction, and A and B are set as arbitrary positive numbers, C is set as an arbitrary real number, and $\alpha$ is set as an arbitrary negative number, the curve rendered by the contour curve is represented as $L = A \cdot (B \cdot x)^\alpha + C$.

* * * * *